United States Patent [19]

Hagen et al.

[11] Patent Number: 5,420,307
[45] Date of Patent: May 30, 1995

[54] 2-AMINO-4-OXO-4H-BENZOPYRANS, THEIR PREPARATAION AND THEIR USE AS ANTIDOTES

[75] Inventors: Helmut Hagen, Frankenthal; Gerhard Nilz, Dannstadt-Schauernheim; Helmut Walter, Obrigheim; Andreas Landes, Limburgerhof; Wolfgang Freund, Neustadt, all of Germany

[73] Assignee: BASF Aktiengesellschaft, Ludwigshafen, Germany

[21] Appl. No.: 70,388

[22] PCT Filed: Nov. 29, 1991

[86] PCT No.: PCT/EP91/02268

§ 371 Date: Jun. 7, 1993

§ 102(e) Date: Jun. 7, 1993

[87] PCT Pub. No.: WO92/10489

PCT Pub. Date: Jun. 25, 1992

[30] Foreign Application Priority Data

Dec. 8, 1990 [DE] Germany .................. 40 39 281.3

[51] Int. Cl.⁶ ............................................. C07D 311/22
[52] U.S. Cl. ................................ 549/401; 549/402
[58] Field of Search ................................ 549/401

[56] References Cited

U.S. PATENT DOCUMENTS

| | | |
|---|---|---|
| 3,932,466 | 1/1976 | Brown et al. . |
| 4,143,042 | 3/1979 | Nohara et al. . |
| 4,255,576 | 3/1981 | Nohara et al. . |
| 4,299,963 | 11/1981 | Nohara et al. . |
| 4,505,738 | 3/1985 | Gsell . |
| 5,059,240 | 10/1991 | Hagen et al. . |

OTHER PUBLICATIONS

A. Nohara et al, Tetrahedron Lett. (1973), 1995–1998.
P. S. Bevan et al., J. Chem. Soc. Perkin Trans. I (1986), pp. 1643–1649.
A. Nohara et al., J. Med. Chem. 28 (1985), pp. 559–568.
Akira Nohara et al., J. Pesticide Sci. 15 (1990) 241–244.
Chemical Abstracts, vol. 108, No. 21, May 23, 1988' abstract No. 186576U, p. 689 Corresponds to JP 62/228,001, (1987).
Chemical Abstracts, vol. 90, No. 7, Feb. 12, 1979; Abst. No. 54827B, p. 599 Corresponds to JP 53/111,071 (1978).
A. Balbi et al., Il Pharmaco 44 (1989), pp. 565–577.
F. Eiden et al., Archiv der Pharmazie 316 (1983), pp. 34–42.
C. K. Ghosh et al., Indian Journal of Chemistry 24B (1985), pp. 914–917.

Primary Examiner—Nicky Chan
Attorney, Agent, or Firm—Keil & Weinkauf

[57] ABSTRACT

2-Amino-4-oxo-4H-benzopyrans I

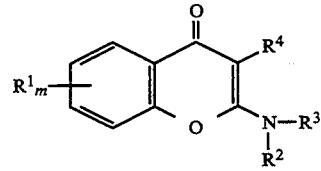

(m=0, 1 or 2; $R^1$–$R^4$ have the meanings stated in the description) and the salts of I, and herbicides which contain 2-(4-hetaryloxy)- and 2-(4-aryloxy)-phenoxyacetic acid derivatives and/or cyclohexenone derivatives as herbicidal active ingredients and 2-amino-4-oxo-4H-benzopyrans I' as antidotes.

2 Claims, No Drawings

2-AMINO-4-OXO-4H-BENZOPYRANS, THEIR PREPARATAION AND THEIR USE AS ANTIDOTES

This application is a 317 of PCT/EP91/02268, filed Nov. 29, 1991.

The present invention relates to 2-amino-4-oxo-4H-benzopyrans of the general formula I.

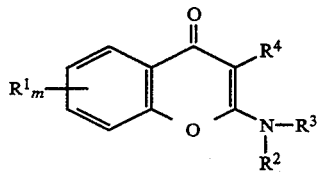

where
- $R^1$ is hydrogen, hydroxyl, halogen, nitro, $C_1$-$C_6$-alkyl, $C_1$-$C_6$-alkoxy, $C_1$-$C_6$-haloalkyl, $C_1$-$C_4$-haloalkoxy, $C_1$-$C_4$-alkyl-thio or a group —$NR^5R^6$,
- $R^5$ is hydrogen or $C_1$-$C_4$-alkyl,
- $R^6$ is hydrogen, $C_1$-$C_4$-alkyl, —CO—$R^7$, —CS—$R^7$ or —$SO_2$—$R^8$,
- $R^7$ is $C_1$-$C_{20}$-alkyl, $C_1$-$C_6$-haloalkyl, $C_3$-$C_8$-cycloalkyl, phenyl-$C_1$-$C_3$-alkyl, amino, $C_1$-$C_4$-alkylamino, di-$C_1$-$C_4$-alkylamino, phenyl or phenylamino where the phenyl radicals are each unsubstituted or carry from one to three of the groups stated for $R^1$,
- $R^8$ is $C_1$-$C_4$-alkyl or is phenyl which may carry from one to three of the groups stated for $R^1$,
- m is 0, 1 or 2, and the radicals $R^1$ may be different when m is 2,
- $R^2$ is hydrogen or $C_1$-$C_4$-alkyl,
- $R^3$ is hydrogen, $C_1$-$C_4$-alkyl or a group —CO—$R^9$, —CS—$R^9$ or —$SO_2R^{10}$,
- $R^9$ has one of the meanings stated under $R^7$,
- $R^{10}$ has one of the meanings stated under $R^8$, or $R^2$ and $R^3$, together with the nitrogen atom to which they are bonded, form a 3-membered to 8-membered saturated or unsaturated ring which, if desired, may in turn furthermore carry from one to three $C_1$-$C_4$-alkyl radicals, or a group =$CR^2R^{11}$,
- $R^{11}$ is hydrogen, hydroxyl, $C_1$-$C_4$-alkyl, $C_1$-$C_8$-alkoxy, $C_3$-$C_8$-cycloalkyl, or benzyl or is phenyl which is unsubstituted or carries from one to three of the groups stated for $R^1$, or is —O—CO—$R^{12}$ or —O—CS—$R^{12}$,
- $R^{12}$ is $C_1$-$C_{20}$-alkyl, $C_1$-$C_6$-haloalkyl, $C_3$-$C_8$-cycloalkyl, phenyl or phenyl-$C_1$-$C_3$-alkyl, where the phenyl radicals may each be unsubstituted or may carry from one to three of the radicals stated for $R^1$,
- $R^4$ is cyano or a group —CO—$R^{13}$, —CS—$R^{13}$ or —CH=N—$R^{14}$,
- $R^{13}$ is hydrogen, $C_1$-$C_6$-alkyl, $C_1$-$C_6$-haloalkyl, amino, $C_1$-$C_4$-alkylamino, di-$C_1$-$C_4$-alkylamino, hydrazino, $C_1$-$C_6$-alkylhydrazino or phenylhydrazino, where the phenyl radical is unsubstituted or substituted by from one to three of the groups stated for $R^1$ and
- $R^{14}$ is one of the radicals $R^{11}$, and the agriculturally useful salts of the compounds I, with the proviso that $R^4$ is not cyano, a group $CONH_2$ or formyl when $R^2$ and $R^3$ are each hydrogen and $R^1$ is simultaneously hydrogen, chlorine, bromine, methyl, methoxy, phenyl, nitro or dimethylamino and m is 1, and furthermore with the proviso that $R^4$ is not a group —CH=N—OH when $R^1$, $R^2$ and $R^3$ are simultaneously hydrogen.

The present invention furthermore relates to processes for the preparation of the compounds I and to herbicides which contain.

A) 2-(4-hetaryloxy)- or 2-(4-aryloxy)-phenoxyacetic or -propionic acid derivatives and/or
B) cyclohexenone derivatives as herbicidal active ingredients and 2-amino-4-oxo-4H-benzopyrans I', where I' has the meanings of I without the proviso, as antidotes, and to methods for selectively controlling undesirable plant growth with these herbicides.

The novel compounds I are obtainable by various methods. 2-Amino-4-oxo-4H-benzopyrans are obtained, for example, by formylating unsubstituted or substituted o-hydroxyacetophenones with phosphoryl chloride and dimethylformamide (H. Harnisch, Liebigs Ann. Chem. 765 (1972), 8; A. Nohara et al., Tetrahedron Lett. 1973, 1995), converting the aldehyde to the oxime and subjecting the latter to an-alkali-catalyzed rearrangement reaction (U. Petersen et al., Liebigs Ann. Chem. 1976, 1659). Another method comprises reacting o-acetoxybenzoyl chlorides with malonodinitrile (G. P. Ellis, J. Chem. Soc. Perkin Trans. I, 1986, 1643). The prior art does not describe a crop-protecting effect of 2-amino-4-oxo-benzopyrans.

It is an object of the present invention to provide compounds which reduce the disadvantages encountered when the abovementioned herbicides of the formulae VIII and IX are used, at least to such an extent that the herbicides are tolerated by the crops from the family comprising the grasses.

We have found that this object is achieved by the 2-amino-4-oxo-4H-benzopyrans I defined at the outset. We have furthermore found processes for the preparation of these compounds I and methods for the joint use of these compounds with the herbicides VIII and IX for influencing undesirable plant growth. The present invention furthermore relates to agents which contain the compounds I', it being unimportant whether the herbicidal active ingredient and the antidote compound are formulated and applied together or separately and, in the case of separate application, the order in which the herbicidal active ingredient and the antidote are applied being irrelevant.

The novel compounds I are obtainable by a plurality of methods. For example, according to the literature cited at the outset, 2-amino-4-oxo-4H-benzopyrans are obtained by formylating a 2-hydroxyacetophenone VI in an inert, aprotic, polar solvent with dimethylformamide/phosphoryl chloride, converting the aldehyde into the oxime and subjecting the latter to a rearrangement reaction under alkaline catalysis to give the o-aminoaldehyde II.

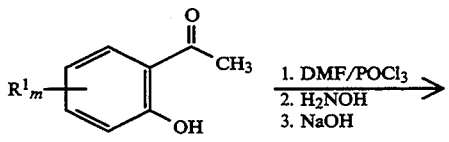

VI

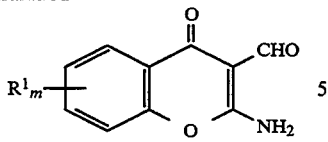

Usually, the starting materials VI and POCl₃ are used in a stoichiometric ratio. However, an excess of one or other may be highly advantageous in specific cases.

The reaction can be carried out continuously or batchwise at atmospheric, superatmospheric or reduced pressure by the conventional methods. The reaction temperature is in general from $-10°$ to $100°$ C., in particular from $0°$ to $40°$ C.

The solvents used are, for example, aliphatic and aromatic chlorohydrocarbons, such as dichloromethane, chloroform and chlorobenzene, or dimethylformamide present in excess.

The synthesis of the compounds in which $R^4$ is CN is carried out, for example starting from the aldehydes ($R^4$=CHO), by reaction with hydroxylammonium chloride in formic acid (P. Kurtz in Houben-Weyl, Methoden der Organischen Chemie), Volume 8, pages 325–330 or Olah, Synthesis 1979, 122).

Triocarboxamides [sic] ($R^4$=—CS—NH₂) are produced by an addition reaction of hydrogen sulfide with the corresponding nitrile ($R^4$=CN) in pyridine/triethylamine as a solvent. Thereafter, $R^{13}$=NH₂ can be substituted by aromatic or aliphaticamines (A. Schöberl in Houben-Weyl, Methoden der Organischen Chemie, Volume 9, page 762–769).

Carboxylic acid derivatives ($R^4$=—CO—$R^{13}$) are obtainable by hydrolyzing the nitriles ($R^4$=CN) and reacting the resulting carboxylic acid with an alcohol or amine. The carboxamide ($R^4$=—CO—NH₂) is obtained by an addition reaction of water with the nitrile ($R^4$=CN) (H. Henecka in Houben-Weyl, Methoden der Organischen Chemie, Volume 8, pages 427–432 and 661–665).

Schiff's bases ($R^4$=—CH=N—$R^{14}$) are obtained, for example, by reacting an aldehyde ($R^4$=CHO) with a primary amine in an aromatic hydrocarbon under acid catalysis and separating off the water of reaction (H. Freytag in Houben-Weyl, Methoden der Organischen Chemie, Volume 11/2, pages 73–98).

The amino groups are derivatized by reacting the 2-aminonitriles ($R^2$ and $R^3$=H; $R^4$=CN) or the 2-aminooxime ($R^2$ and $R^3$=H; $R^4$=—CH=NOH) with an anhydride or an acyl chloride (H. Henecka in Houben-Weyl, Methoden der Organischen Chemie, Volume 8, pages 655–658).

In view of the intended use of the compounds I as crop protection agents, suitable substituents are the following:

m is 0, 1 or 2, and the radicals $R^1$ may be different when m is 2;

$R^1$ is hydrogen, hydroxyl, nitro, halogen, such as fluorine, chlorine, bromine or iodine, in particular chlorine or bromine, $C_1$–$C_6$-alkyl, such as methyl, ethyl, n-propyl, 1-methylethyl, n-butyl, 1-methylpropyl or 1,1-dimethylethyl, particularly preferably methyl or ethyl, $C_1$–$C_6$-alkoxy, such as methoxy, ethoxy, n-propoxy, 1-methylethoxy, n-butoxy, 1-methylpropoxy, 2-methylpropoxy or hexyloxy, in particular methoxy or ethoxy, $C_1$–$C_6$-haloalkyl, in particular $C_1$- or $C_2$-haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, particularly preferably trichloromethyl or trifluoromethyl, $C_1$–$C_4$-haloalkoxy, in particular $C_1$- or $C_2$-haloalkoxy, such as difluoromethoxy, trifluoromethoxy, chloridifluoromethoxy, dichlorofluoromethoxy, 1-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, particularly preferably 2,2,2-trifluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio, or a group $NR^5R^6$, $R^5$ is hydrogen or $C_1$–$C_4$-alkyl, such as methyl, ethyl, isopropyl or tert-butyl, $R^6$ is hydrogen, $C_1$–$C_4$-alkyl, such as methyl, ethyl, isopropyl or tert-butyl, —CO—$R^7$, —CS—$R^7$ or —SO₂—$R^8$, $R^7$ is $C_1$–$C_{20}$-alkyl as stated for $R^1$, or octyl, dodecyl, hexadecyl or octadecyl, preferably $C_1$–$C_4$-alkyl, in particular methyl or ethyl, haloalkyl as stated for $R^1$, $C_3$–$C_8$-cycloalkyl, such as cyclopropyl, cyclobutyl, cyclopentyl, cyclohexyl, cycloheptyl or cyclooctyl, in particular cyclohexyl, phenyl-$C_1$–$C_3$-alkyl, such as benzyl, 2-phenylethyl or 3-phenylpropyl, preferably benzyl, amino which may carry one or two of the alkyl radicals stated for $R^1$, in particular methyl, where these radicals may be different in the case of disubstituted amino, in particular methylbenzylamino, aminophenyl where the aromatic ring may carry from one to three of the groups stated for $R^1$, or phenyl which may carry from one to three of the groups stated for $R^1$, $R^8$ is $C_1$–$C_4$-alkyl as stated for $R^1$, in particular methyl or ethyl, or phenyl which may carry from one to three groups stated for $R^1$, $R^2$ is hydrogen or $C_1$–$C_4$-alkyl, such as methyl, ethyl, n-propyl, isopropyl, n-butyl or tert-butyl, preferably methyl or ethyl, $R^3$ is hydrogen, $C_1$–$C_4$-alkyl, such as methyl, ethyl, n-propyl, isopropyl, n-butyl or tert-butyl, preferably methyl or ethyl, a group —CO—$R^9$ or —CS—$R^9$, in particular —CO—(C-1-$C_6$-alkyl), or a group —SO₂—$R^{10}$, in particular —SO₂—CH₃, —SO₂C₂H₅ or —SO₂C₆H₅, $R^9$ is $C_1$–$C_{20}$-alkyl as stated for $R^1$ or octyl, dodecyl, hexadecyl or octadecyl, preferably $C_1$–$C_6$-alkyl, in particular methyl or ethyl, haloalkyl as stated for $R^1$, $C_3$–$C_8$-cycloalkyl, such as cyclopropyl, cyclobutyl, cyclopentyl, cyclohexyl, cycloheptyl or cyclooctyl, in particular cyclohexyl, phenyl-$C_1$–$C_4$-alkyl, such as phenylmethyl, 2-phenylethyl or 3-phenylpropyl, in particular phenylmethyl, amino which may carry one or two of the alkyl radicals stated for $R^1$, in particular methyl, where these radicals may be different in the case of disubstituted amino, in particular methylbenzylamino, aminophenyl where the aromatic ring may carry from one to three of the groups stated for $R^1$, or phenyl which may carry from one to three of the groups stated for $R^1$, $R^{10}$ is $C_1$–$C_4$-alkyl as stated for $R^1$, in particular methyl or ethyl, or phenyl which may carry from one to three of the groups stated for $R^1$, $R^4$ is cyano or a group —CO—$R^{13}$, —CS—$R^{13}$ or —CH=N—$R^{14}$, $R^{13}$ is hydrogen, alkyl or haloalkyl as stated for $R^1$, in particular methyl or ethyl, trifluoromethyl or trichloromethyl, amino which may carry one or two of the alkyl radicals stated for $R^1$, in particular methyl, where these radicals may be different in the case of disubstituted amino, in particular methylbenzylamino, or hydrazino which may be substituted by one of the groups stated for $R^2$ or by phenyl which may carry from one to three of the groups stated for $R^1$, or $R^2$ and $R^3$ together with the common nitrogen atom to which they are bonded, form a 3-membered to 8-membered, in particular 5-membered or 6-membered, saturated or unsaturated ring which is unsubstituted or substituted by from one to three $C_1$–$C_4$-alkyl groups, e.g. methyl, for example piperidyl or unsubstituted or substituted pyrrolyl, which is obtainable by reacting the amine ($R^2$ and $R^3$=H) with an unsubstituted or substituted 2,5-dimethoxytetrahydrofuran or 1,4-diketone, such as acetonylacetone (Robba, Chem. Pharm. Bull. 33 (1985), 2798), or a group =$CR^2R^{11}$, $R^{11}$ is hydrogen, hydroxyl, $C_3$–$C_8$-cycloalkyl, such as cyclopropyl, cyclopentyl, cyclohexyl, cycloheptyl or cyclooctyl, in particular cyclohexyl, phenyl which may carry from one to three of the groups stated for $R^1$, benzyl, $C_1$–$C_4$-alkyl, such as methyl, ethyl, n-propyl, isopropyl, n-butyl or tert-butyl, preferably methyl or ethyl, $C_1$–$C_6$-alkoxy as stated for $R^1$, or a group —O—CO—$R^{12}$ or —O—C-S—$R^{12}$, and $R^{12}$ is $C_1$–$C_{20}$-alkyl as stated for $R^1$, or n-octyl, dodecyl, hexadecyl or octadecyl, in particular $C_1$–$C_6$-alkyl as stated for $R^1$, preferably methyl or ethyl, haloalkyl as stated for $R^1$, in particular chloroethyl, $C_3$–$C_8$-cycloalkyl, such as cyclopropyl, cyclopentyl, cyclohexyl, cycloheptyl or cyclooctyl, in particular cyclohexyl, phenyl-$C_1$–$C_3$-alkyl, such as benzyl, 2-phenylethyl or 3-phenylpropyl, preferably benzyl, or phenyl which may carry from one to three of the radicals stated for $R^1$;

Suitable salts of the compound I are agriculturally useful salts, for example alkali metal salts, in particular the potassium or sodium salt, alkaline earth metal salts, in particular the calcium, magnesium or barium salt, manganese, copper, zinc or iron salts and ammonium, phosphonium and tetraalkylammonium salts, benzyltrialkylammonium salts, trialkylsulfonium salts or trialkylsulfoxonium salts.

The 2-amino-4-oxo-4H-benzopyrans I and I' are suitable as antidotes for ensuring that herbicidal active ingredients are better tolerated by crops such as millet, rice, corn, cereal species (wheat, rye, barley and oats), cotton, sugar beet, sugar cane and soyabean. They have an antagonistic effect on herbicides from a very wide range of classes, such as triazines, phenyl urea derivatives, carbamates, thiocarbamates, haloacetanilides, benzoic acid derivatives and in particular halophenoxyacetates, substituted phenoxyphenoxyacetates, phenoxyphenoxypropionates and cyclohexenone derivatives.

Herbicidal active ingredients from the group consisting of the 2-(4-hetaryloxy)- or 2-(4-aryloxy)phenoxyacetic acid derivatives of the formula VIII,

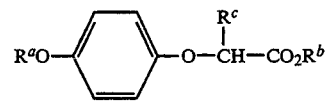

where $R^a$ is a phenyl ring, a pyridyl ring, benzoxazyl, benzothiazyl or benzopyrazinyl, where these aromatic ring systems may carry up to two of the following radicals: halogen, nitro, $C_1$–$C_4$-alkyl, $C_1$–$C_4$-haloalkyl and/or $C_1$–$C_4$-haloalkoxy, $R^b$ is hydrogen, $C_1$–$C_4$-alkyl or one equivalent of a plant-tolerated cation and $R^c$ is hydrogen or methyl, are disclosed in the literature, for example in DE-A-22 23 894, DE-A-24 33 067, DE-A-25 76 251, DE-A-30 04 770, BE-A-868 875 and BE-A-858 618.

They are used for controlling undesirable plants from the Gramineae family. However, the toleration of these substances by crops varies from commercially acceptable to nontolerated, depending on the substituents and application rate.

The same situation is encountered in the case of cyclohexenone derivatives of the formula IX

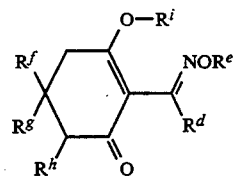

where $R^d$ is $C_1$–$C_4$-alkyl, such as methyl, ethyl, n-propyl, isopropyl, n-butyl or tert-butyl, preferably ethyl or n-propyl, $R^e$ is $C_1$–$C_4$-alkyl, such as methyl, ethyl, n-propyl, isopropyl, n-butyl or tert-butyl, preferably ethyl or n-propyl, $C_3$- or $C_4$-alkenyl, preferably prop-2-enyl, $C_3$- or $C_4$-alkynyl or $C_3$- or $C_4$-haloalkenyl, preferably 3-chloroprop-2-en-1-yl, a $C_1$–$C_4$-alkylene or $C_1$–$C_4$-alkenylene chain, both of which may furthermore carry from one to three $C_1$–$C_3$-alkyl radicals and/or halogen atoms, or a 3-membered to 6-membered alkylene or 4-membered to 6-membered alkenylene chain which, if desired, is substituted by $C_1$–$C_3$-alkykl and each of which contains, as a chain member, an oxygen or sulfur atom which is not directly adjacent to the oxime ether moiety, all abovementioned chains carrying, as a terminal group, the phenyl ring which in turn may be substituted by from one to three radicals selected from the group consisting of a benzyloxycarbonyl or phenyl radical and from one to three of each of the following radicals: nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring additionally to carry a number of halogen atoms such that the total number of radicals is 4 or 5; 4-(p-fluorophenyl)-but-3-enyl, 4-(p-chlorophenyl)-but-3-enyl and 2-(p-chlorophenoxy)-propyl are particularly preferred; or the thienyl group which may furthermore carry a halogen atom, $R^f$ is $C_1-C_4$-alkyl as stated for $R^d$, which may be monosubstituted to disubstituted by $C_1-C_4$-alkylthio or $C_1-C_4$-alkoxy, a 5-membered to 6-membered saturated or monounsaturated ring system which, in addition to carbon members, may contain an oxygen atom, a sulfur atom or a sulfoxyl or sulfonyl group, preferably tetrahydropyranyl, dihydropyranyl or tetrahydrothiopyranyl, where the ring system may furthermore carry from one to three radicals selected from the group consisting of hydroxyl, halogen, $C_1-C_4$-alkyl, $C_1-C_4$-haloalkyl, $C_1-C_4$-alkoxy and $C_1-C_4$-alkylthio, a 10-membered saturated or monounsaturated heterocyclic structure which contains two nonadjacent oxygen atoms or sulfur atoms and may be substituted by up to three $C_1-C_4$-alkyl groups and/or methoxy groups, or phenyl, pyridyl, thiazolyl, pyrazolyl, pyrrolyl or isoxazolyl, where each of these groups can, if desired, furthermore carry from one to three radicals selected from the group consisting of $C_1-C_4$-alkyl, $C_1-C_4$-haloalkyl, $C_1-C_4$-alkoxy, $C_1-C_4$-alkylthio, $C_3-C_6$-alkenyloxy, $C_3-C_6$-alkynyloxy, $C_1-C_4$-alkoxy-$C_1-C_3$-alkyl, $C_1-C_4$-dialkoxy-$C_1-C_3$-alkyl, formyl, halogen and benzoylamino, $R^g$ is hydrogen or hydroxyl or, if $R^f$ is $C_1-C_6$-alkyl, $R^g$ is $C_1-C_6$-alkyl, preferably hydrogen, $R^h$ is hydrogen, cyano, halogen, $C_1-C_4$-alkoxycarbonyl or $C_1-C_4$-alkylketoxime, preferably hydrogen, and $R^i$ is hydrogen or one equivalent of an agriculturally useful cation.

They are likewise described in the literature (for example EP-A 228 598, EP-A 230 235, EP-A 238 021, EP-A 368 227, U.S. Pat No. 4,432,786, DE-A 24 39 104, DE-A 40 14 986 and DE-A 40 33 423) as herbicides and are used predominantly for controlling undesirable grasses in dicotyledon crops and in grasses which do not belong to the Gramineae family. Depending on the structure of the substituents and the dose used, compounds from this group can also be employed for selectively controlling undesirable grasses in gramineous crops, such as wheat and rice.

Cyclohexenone derivatives of the formula IX in which $R^e$ is unsubstituted or substituted alkyl- or alkenylphenyl, for example butyl- or butenylphenyl, can be prepared in a conventional manner from known derivatives of the formula X (EP-A-80 301, EP-A-125 094, EP-A 142 741, U.S. Pat. No. 4,249,937, EP-A 137 174 and EP-A 177 913) and the corresponding hydroxylamines of the formula XI (Houben-Weyl, 10/1, page 1181 et seq.) (EP-A 169 521).

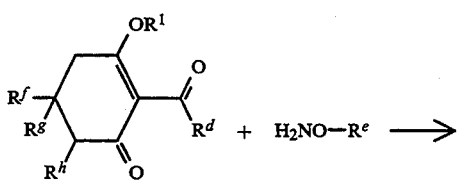

X      XI

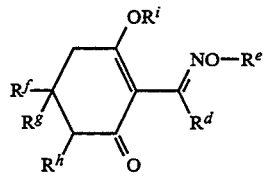

IX

The reaction is advantageously carried out in the heterogeneous phase in a solvent at an adequate temperature below about 80° C. in the presence of a base, and the hydroxylamine XI is used in the form of its ammonium salt.

Examples of suitable bases are carbonates, bicarbonates, acetates, alcoholates or oxides of alkali or alkaline earth metals, in particular sodium hydroxide, potassium hydroxide, magnesium oxide and calcium oxide. Organic bases, such as pyridine or tertiary amines, may also be used. The base is added, for example, in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The product can be isolated, for example, by evaporating down the mixture, partitioning the residue between methylene chloride and water and distilling off the solvent under reduced pressure.

However, the free hydroxylamine base, for example in the form of an aqueous solution, can also be used directly for this reaction; depending on the solvent used for the compound X, a one-phase or two-phase reaction mixture is obtained.

Suitable solvents for this variant are, for example, alcohols, such as methanol, ethanol, isopropanol or cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds IX can be obtained by treating the 3-hydroxy compounds with sodium hydroxide, potassium hydroxide or a sodium or potassium alcoholate in aqueous solution or in an organic solvent, such as methanol, ethanol, acetone and toluene.

Other metal salts, such as manganese, copper, zinc, iron, calcium, magnesium and barium salts, can be prepared from the sodium salts in a conventional manner, as can ammonium and phosphonium salts by means of ammonia or ammonium, phosphonium, sulfonium or sulfoxonium hydroxides.

The compounds of type X can be prepared, for example from the corresponding cyclohexane-1,3-diones of the formula XII

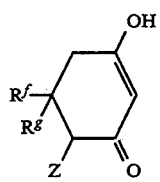

where Z is hydrogen or methoxycarbonyl and $R^g$ is hydrogen, by known methods (Tetrahedron Lett. (1975), 2491).

It is also possible to prepare the compounds of the formula X via the enol ester intermediates, which are obtained in the reaction of compounds of the formula XII with acyl chlorides in the presence of bases and are subsequently subjected to a rearrangement reaction with certain imidazole or pyridine derivatives (Japanese Preliminary Published Application 79/063 052).

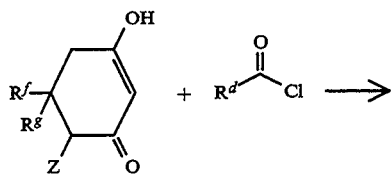

The compounds of the formula XII are obtained via a number of known process steps, starting from known intermediates.

The synthesis of the hydroxylamines XI in which $R^e$ is unsubstituted or substituted phenylbutyl is carried out according to the reaction scheme below, for example by α) alkylation of cyclic hydroximides XIII with suitable phenylbutyl halides and subsequent elimination of the protective groups, for example with hydrazine or ethanolamine, similarly to Examples from EP-A-244 786 or Houben-Weyl, Methoden der organischen Chemie, Volume X/1, page 1152 et seq.

β) hydrogenation of N-4-phenylbutenyloxyphthalimides, the preparation of which is described in DE-A 38 38 310, by means of suitable catalysts, for example palladium on active carbon, in suitable inert solvents, eg. methanol, tetrahydrofuran or dioxane, and subsequent elimination of the protective groups as described above.

The hydrogenation is advantageously carried out at from 20° C. to the boiling point of the solvent, in particular at room temperature, at atmospheric, superatmospheric or reduced pressure, by the conventional methods. A pressure range of from 1 to 10, in particular from 1 to 2, bar is preferred.

Reaction scheme:

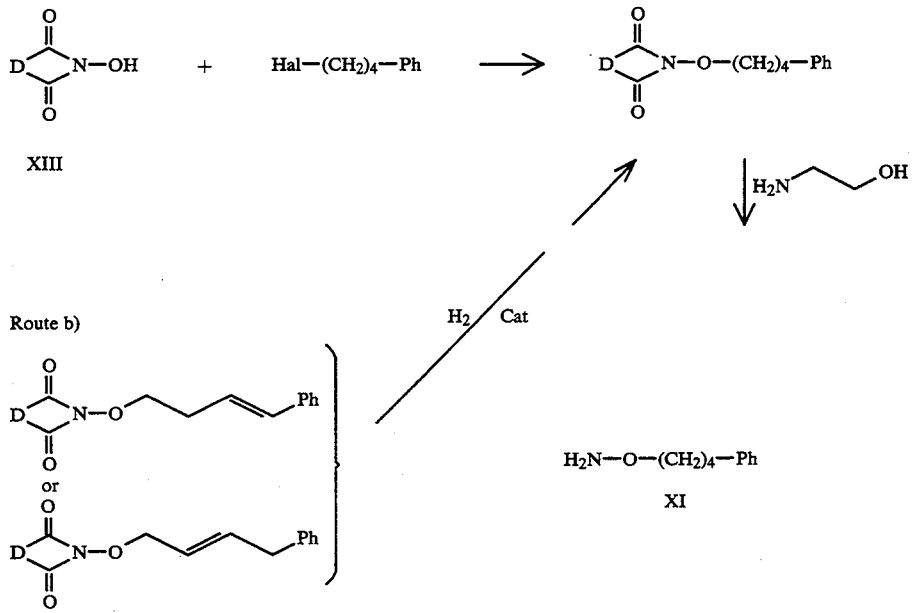

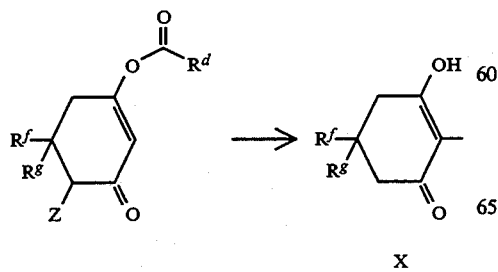

Ph = unsubstituted or substituted phenyl

Examples of suitable cyclic hydroximides XIII are the following substances:

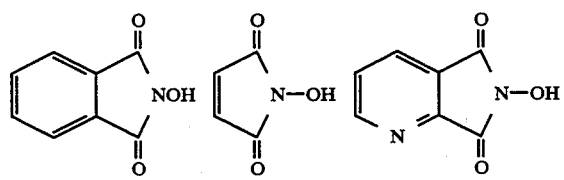

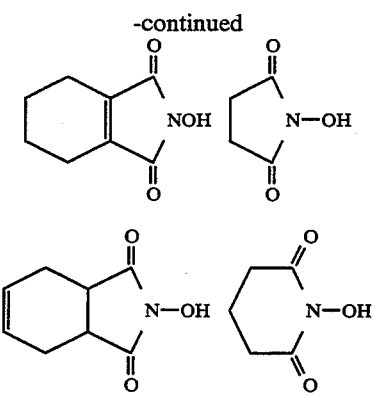

The synthesis of the hydroxylamines XI in which $R^e$ is unsubstituted or substituted butenylphenyl, where the phenyl radical abbreviated below to Ph may in turn be substituted or unsubstituted, is carried out according to the following reaction scheme, starting from aniline derivatives, by diazotization and subsequent coupling of the diazonium salt to an appropriately substituted butadiene XIV. The resulting mixture of XVa and XVb is coupled to a cyclic hydroximide XVII, and the protected hydroxylamine derivative XVI obtained is converted into the free hydroxylamine XI by cleavage with 2-aminoethanol:

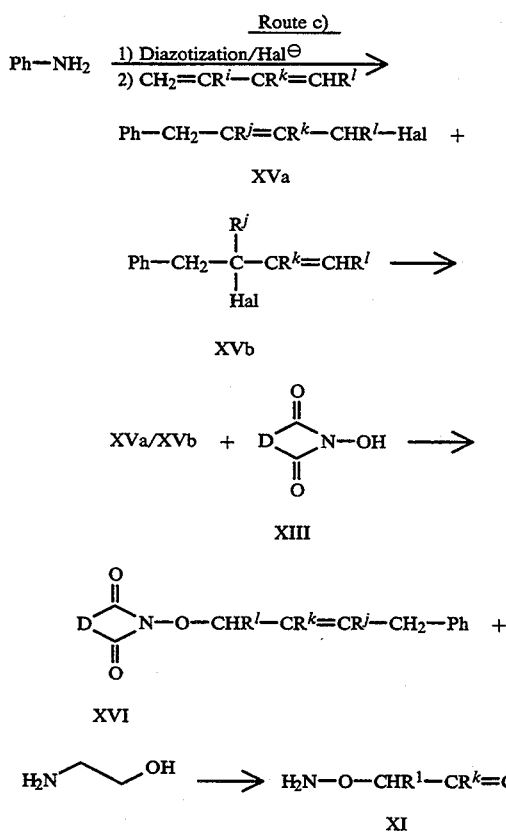

$R^j$, $R^k$ and $R^l$ independently of one another are each hydrogen, $C_1$–$C_3$-alkyl and/or halogen. Hal is halogen, preferably chlorine.

The halides XVa required for the above synthesis of the hydroxylamines of the formula XI can be prepared, as a mixture with XVb, by processes known from the literature, for example by reacting diazonium salts of aromatic and heteroaromatic anilines with dienes. The range of uses of the reaction is discussed in Organic Reactions 11 (1960), 189 and 24 (1976), 225.

Coupling of the isomeric halides XVa and XVb to a cyclic hydroximide of the formula XIII gives exclusively the cyclic imidoethers of the formula XVI which, after elimination of the protective group on the nitrogen, give the hydroxylamines XI.

The reaction with hydroximide XIII (route a and c) is carried out in the presence of an acid acceptor and of a solvent. For cost reasons, hydroxyphthalimide is preferably used as the hydroximide XIII.

Suitable acid acceptors are alkali metal carbonates, such as potassium carbonate or sodium carbonate, alkali metal bicarbonates, such as potassium bicarbonate and sodium bicarbonate, tertiary amines, such as trimethylamine and triethylamine, and basic heterocycles, such as pyridine. For cost reasons, potassium carbonate and sodium carbonate are preferred.

Suitable solvents are aprotic dipolar organic solvents, eg. dimethylformamide, dimethyl sulfoxide and/or sulfolane.

Alkylation under phase transfer conditions is also possible. Water-immiscible compounds, such as hydrocarbons or chlorohydrocarbons, are used as organic solvents here. Suitable phase transfer catalysts are quaternary ammonium and phosphonium salts.

The cyclic imidoethers XVI are cleaved with alkanolamines by a method similar to that described in EP-A 244 786. In this process, the hydroxylamines XI can be isolated as free bases or, after precipitation with acids, in the form of salts. Readily crystallizing salts are obtained by reacting the bases with oxalic acid.

Specific examples of herbicidal hetaryloxy- or aryloxyphenoxyacetic acid derivatives of the formula VIII whose toleration by crops can be improved by means of 2-amino-4-oxo-4H-benzopyrans of the formula I or I' are shown in Table 1 below.

TABLE 1

VIII: $R^a$—O—[phenyl]—O—CH($R^c$)—CO$_2R^b$

| No. | $R^a$ | $R^b$ | $R^c$ | Reference |
|---|---|---|---|---|
| 1.01 | 3,4-dichlorophenyl | CH$_3$ | CH$_3$ | DE-A 22 23 894 |
| 1.02 | 5-(trifluoromethyl)pyridin-2-yl | n-C$_4$H$_9$ | CH$_3$ | BE-A 868 875 |
| 1.03 | 2-(4-chlorophenoxy)... | C$_2$H$_5$ | CH$_3$ | BE-A 858 618 |
| 1.04 | 5-(trifluoromethyl)-3-chloropyridin-2-yl | CH$_3$ | CH$_3$ | BE-A 868 875 |

TABLE 1-continued

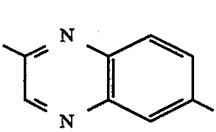

| No. | $R^a$ | $R^b$ | $R^c$ | Reference |
|---|---|---|---|---|
| 1.05 | (3-methyl-7-chloroquinoxalin-2-yl) | $C_2H_5$ | $CH_3$ | DE-A 30 04 770 |

Specific examples of cyclohexenones of the formula IX whose toleration by crops can be improved by 2-amino-4-oxo-4H-benzopyrans I and I' are shown in Tables 2 to 13 below.

TABLE 2

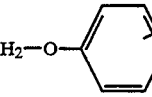

IX ($R^e = -CH_2CH_2-O-\text{phenyl}$); $R^g, R^h, R^i = H$

| No. | $R^d$ | $R^f$ | Radicals on phenyl ring | Physical data/$^1$H-NMR [δ in ppm], m.p. [C.] |
|---|---|---|---|---|
| 2.01 | Ethyl | Tetrahydropyran-3-yl | — | 42–45 |
| 2.02 | Propyl | Tetrahydropyran-3-yl | — | 3.90(m, 2H), 4.20(t, 2H), 4.40(m, 2H), 6.80–7.00(m, 3H), 7.13–7.37(m, 2H) |
| 2.03 | Ethyl | Tetrahydropyran-4-yl | — | 106–107 |
| 2.04 | Propyl | Tetrahydropyran-4-yl | — | 72–73 |
| 2.05 | Ethyl | Tetrahydrothiopyran-3-yl | — | 52–55 |
| 2.06 | Propyl | Tetrahydrothiopyran-3-yl | — | 92 |
| 2.07 | Ethyl | Tetrahydropyran-3-yl | 2-F | 76–78 |
| 2.08 | Propyl | Tetrahydropyran-3-yl | 2-F | 72–77 |
| 2.09 | Ethyl | Tetrahydropyran-4-yl | 2-F | 121–125 |
| 2.10 | Propyl | Tetrahydropyran-4-yl | 2-F | 103–107 |
| 2.11 | Ethyl | Tetrahydrothiopyran-3-yl | 2-F | 82–86 |
| 2.12 | Propyl | Tetrahydrothiopyran-3-yl | 2-F | 81–85 |
| 2.13 | Ethyl | Tetrahydropyran-3-yl | 3-F | 62–68 |
| 2.14 | Propyl | Tetrahydropyran-3-yl | 3-F | 3.90(m, 2H), 4.20(t, 2H), 4.40(m, 2H) 6.70(m, 3H), 7.25(m, 1H), |
| 2.15 | Ethyl | Tetrahydropyran-4-yl | 3-F | 103–109 |
| 2.16 | Propyl | Tetrahydropyran-4-yl | 3-F | 73–79 |
| 2.17 | Ethyl | Tetrahydrothiopyran-3-yl | 3-F | 4.20(t, 2H), 4.40(m, 2H) |
| 2.18 | Propyl | Tetrahydrothiopyran-3-yl | 3-F | 6.70(m, 3H), 7.25(m, 1H) |
| 2.19 | Ethyl | Tetrdhydropyran-3-yl | 4-F | 64–67 |
| 2.20 | Propyl | Tetrahydropyran-3-yl | 4-F | 70–72 |
| 2.21 | Ethyl | Tetrahydropyran-4-yl | 4-F | 101–103 |
| 2.22 | Propyl | Tetrahydropyran-4-yl | 4-F | 107–109 |
| 2.23 | Ethyl | Tetrahydrothiopyran-3-yl | 4-F | 105–108 |
| 2.24 | Propyl | Tetrahydrothiopyran-3-yl | 4-F | 82–84 |
| 2.25 | Ethyl | Tetrahydropyran-3-yl | 2-Cl | 74–80 |
| 2.26 | Propyl | Tetrahydropyran-3-yl | 2-Cl | 67–71 |
| 2.27 | Ethyl | Tetrahydropyran-4-yl | 2-Cl | 4.00(m, 2H), 4.27(t, 2H), 4.47(m, 2H), 7.20(t, 1H), 7.37(d, 1H) |
| 2.28 | Propyl | Tetrahydropyran-4-yl | 2-Cl | 68–72 |
| 2.29 | Ethyl | Tetrahydrothiopyran-3-yl | 2-Cl | 74–78 |
| 2.30 | Propyl | Tetrahydrothiopyran-3-yl | 2-Cl | 72–78 |
| 2.31 | Ethyl | Tetrahydropyran-3-yl | 3-Cl | |
| 2.32 | Propyl | Tetrahydropyran-3-yl | 3-Cl | |
| 2.33 | Ethyl | Tetrahydropyran-4-yl | 3-Cl | |
| 2.34 | Propyl | Tetrahydropyran-4-yl | 3-Cl | |
| 2.35 | Ethyl | Tetrahydrothiopyran-3-yl | 3-Cl | |
| 2.36 | Propyl | Tetrahydrothiopyran-3-yl | 3-Cl | |
| 2.37 | Ethyl | Tetrahydropyran-3-yl | 4-Cl | 3.93(m, 2H), 4.20(t, 2H), 4.43(m, 2H), 6.90(m, 2H), 7.25(m, 2H) |
| 2.38 | Propyl | Tetrahydropyran-3-yl | 4-Cl | 3.93(m, 2H), 4.20(t, 2H), 4.43(m, 2H), 6.90(m, 2H), 7.25(m, 2H) |
| 2.39 | Ethyl | Tetrahydropyran-4-yl | 4-Cl | 116–118 |
| 2.40 | Propyl | Tetrahydropyran-4-yl | 4-Cl | 104–106 |
| 2.41 | Ethyl | Tetrahydrothiopyran-3-yl | 4-Cl | 74–77 |
| 2.42 | Propyl | Tetrahydrothiopyran-3-yl | 4-Cl | 86–88 |
| 2.43 | Ethyl | Tetrahydropyran-3-yl | 2-$CF_3$ | |
| 2.44 | Propyl | Tetrahydropyran-3-yl | 2-$CF_3$ | |
| 2.45 | Ethyl | Tetrahydropyran-4-yl | 2-$CF_3$ | |
| 2.46 | Propyl | Tetrahydropyran-4-yl | 2-$CF_3$ | |
| 2.47 | Ethyl | Tetrahydrothiopyran-3-yl | 2-$CF_3$ | |

TABLE 2-continued

Structure: IX ($R^e$ = —CH$_2$CH$_2$—O—phenyl with Radicals); $R^g$, $R^h$, $R^i$ = H

| No. | $R^d$ | $R^f$ | Radicals on phenyl ring | Physical data/$^1$H-NMR [δ in ppm], m.p. [°C] |
|---|---|---|---|---|
| 2.48 | Propyl | Tetrahydrothiopyran-3-yl | 2-CF$_3$ | |
| 2.49 | Ethyl | Tetrahydropyran-3-yl | 3-CF$_3$ | |
| 2.50 | Propyl | Tetrahydropyran-3-yl | 3-CF$_3$ | |
| 2.51 | Ethyl | Tetrahydropyran-4-yl | 3-CF$_3$ | |
| 2.52 | Propyl | Tetrahydropyran-4-yl | 3-CF$_3$ | |
| 2.53 | Ethyl | Tetrahydrothiopyran-3-yl | 3-CF$_3$ | |
| 2.54 | Propyl | Tetrahydrothiopyran-3-yl | 3-CF$_3$ | |
| 2.55 | Ethyl | Tetrahydropyran-3-yl | 4-CF$_3$ | 72–77 |
| 2.56 | Propyl | Tetrahydropyran-3-yl | 4-CF$_3$ | 3.90(m, 2H), 4.27(t, 2H), 4.47(m, 2H) 7.00(d, 2H), 7.55(d, 2H) |
| 2.57 | Ethyl | Tetrahydropyran-4-yl | 4-CF$_3$ | |
| 2.58 | Propyl | Tetrahydropyran-4-yl | 4-CF$_3$ | 90–94 |
| 2.59 | Ethyl | Tetrahydrothiopyran-3-yl | 4-CF$_3$ | 73–79 |
| 2.60 | Propyl | Tetrahydrothiopyran-3-yl | 4-CF$_3$ | 4.27(t, 2H), 4.47(m, 2H), 7.00(d, 2H) 7.55(d, 2H) |
| 2.61 | Ethyl | Tetrahydropyran-3-yl | 2,4-Cl$_2$ | 73–75 |
| 2.62 | Propyl | Tetrahydropyran-3-yl | 2,4-Cl$_2$ | 69–73 |
| 2.63 | Ethyl | Tetrahydropyran-4-yl | 2,4-Cl$_2$ | 4.00(m, 2H), 4.25(t, 2H), 4.45(t, 2H) 6.87(d, 1H), 7.17(d, 1H), 7.37(d, 1H) |
| 2.64 | Propyl | Tetrahydropyran-4-yl | 2,4-Cl$_2$ | 4.00(m, 2H), 4.25(t, 2H), 4.45(t, 2H) 6.87(d, 1H), 7.17(d, 1H), 7.37(d, 1H) |
| 2.65 | Ethyl | Tetrahydrothiopyran-3-yl | 2,4-Cl$_2$ | 4.25(t, 2H), 4.45(t, 2H), 6.87(d, 1H) 7.17(d, 1H), 7.37(d, 1H) |
| 2.66 | Propyl | Tetrahydrothiopyran-3-yl | 2,4-Cl$_2$ | 4.25(t, 2H), 4.45(t, 2H), 6.87(d, 1H) 7.17(d, 1H), 7.37(d, 1H) |
| 2.67 | Ethyl | Tetrahydropyran-3-yl | 2,4,6-Cl$_3$ | 90–93 |
| 2.68 | Propyl | Tetrahydropyran-3-yl | 2,4,6-Cl$_3$ | 83–87 |
| 2.69 | Ethyl | Tetrahydropyran-4-yl | 2,4,6-Cl$_3$ | 79–82 |
| 2.70 | Propyl | Tetrahydropyran-4-yl | 2,4,6-Cl$_3$ | 4.00(m, 2H), 4.27(t, 2H), 4.45(m, 2H), 7.32(s, 2H) |
| 2.71 | Ethyl | Tetrahydrothiopyran-3-yl | 2,4,6-Cl$_3$ | 105–108 |
| 2.72 | Propyl | Tetrahydrothiopyran-3-yl | 2,4,6-Cl$_3$ | 4.27(t, 2H), 4.45(m, 2H), 7.82(s, 2H) |
| 2.73 | Ethyl | Tetrahydropyran-3-yl | 4-NO$_2$ | 3.90(m, 2H), 4.32(m, 2H), 4.50(m, 2H), 7.00(d, 2H), 8.20(d, 2H) |
| 2.74 | Propyl | Tetrahydropyran-3-yl | 4-NO$_2$ | 3.90(m, 2H), 4.32(m, 2H), 4.50(m, 2H) 7.00(d, 2H), 8.20(d, 2H) 126–129 |
| 2.75 | Ethyl | Tetrahydropyran-4-yl | 4-NO$_2$ | 138–141 |
| 2.76 | Propyl | Tetrahydropyran-4-yl | 4-NO$_2$ | 4.32(m, 2H), 4.50(m, 2H), 7.00(d, 2H), 8.20(d, 2H) |
| 2.77 | Ethyl | Tetrahydrothiopyran-3-yl | 4-NO$_2$ | |
| 2.78 | Propyl | Tetrahydrothiopyran-3-yl | 4-NO$_2$ | 4.32(m, 2H), 4.50(m, 2H), 7.00(d, 2H) 8.20(d, 2H) |

TABLE 3

Structure: IX ($R^e$ = —CH$_2$CH(CH$_3$)—O—phenyl with Radicals); $R^g$, $R^h$, $R^i$ = H

| No. | $R^d$ | $R^f$ | Radicals on phenyl ring | Physical data/$^1$H-NMR [δ in ppm], mp. [°C] |
|---|---|---|---|---|
| 3.01 | Ethyl | Tetrahydropyran-3-yl | — | |
| 3.02 | Propyl | Tetrahydropyran-3-yl | — | |
| 3.03 | Ethyl | Tetrahydropyran-4-yl | — | |
| 3.04 | Propyl | Tetrahydropyran-4-yl | — | |
| 3.05 | Ethyl | Tetrahydrothiopyran-3-yl | — | |
| 3.06 | Propyl | Tetrahydrothiopyran-3-yl | — | |
| 3.07 | Ethyl | Tetrahydropyran-3-yl | 4-F | |
| 3.08 | Propyl | Tetrahydropyran-3-yl | 4-F | |
| 3.09 | Ethyl | Tetrahydropyran-4-yl | 4-F | |
| 3.10 | Propyl | Tetrahydropyran-4-yl | 4-F | |
| 3.11 | Ethyl | Tetrahydrothiopyran-3-yl | 4-F | |
| 3.12 | Propyl | Tetrahydrothiopyran-3-yl | 4-F | |
| 3.13 | Ethyl | Tetrahydropyran-3-yl | 4-Cl | |

TABLE 3-continued

[Structure: cyclohexenone with OH, R^f substituent, =N-O-CH2CH(CH3)-O-phenyl-Radicals, R^d; IX (R^e = —CH₂CH(CH₃)—O—phenyl—Radicals; R^g, R^h, R^i = H)]

| No. | R^d | R^f | Radicals on phenyl ring | Physical data/¹H-NMR [δ in ppm], mp. [°C.] |
|---|---|---|---|---|
| 3.14 | Propyl | Tetrahydropyran-3-yl | 4-Cl | |
| 3.15 | Ethyl | Tetrahydropyran-4-yl | 4-Cl | 1.35(m, 3H), 4.05–4.30(m, 2H), 4.60(m, 1H), 6.80–7.40(m, 4H) |
| 3.16 | Propyl | Tetrahydropyran-4-yl | 4-Cl | 1.35(m, 3H), 4.05–4.30(m, 2H), 4.60(m, 1H), 6.80–7.40(m, 4H) |
| 3.17 | Ethyl | Tetrahydrothiopyran-3-yl | 4-Cl | 1.35(m, 3H), 4.05–4.25(m, 2H), 4.60(m, 1H), 6.80–7.40(m, 4H) |
| 3.18 | Propyl | Tetrahydrothiopyran-3-yl | 4-Cl | 1.35(m, 3H), 4.05–4.30(m, 2H), 4.60(m, 1H), 6.80–7.40(m, 4H) |

TABLE 4

[Structure: cyclohexenone with OH, R^f substituent, =N-O-CH2CH2-S-phenyl-Radicals, R^d; IX (R^e = —CH₂CH₂—S—phenyl—Radicals; R^g, R^h, R^i = H)]

| No. | R^d | R^f | Radicals on phenyl ring | Physical data/¹H-NMR [δ in ppm], mp. [°C.] |
|---|---|---|---|---|
| 4.01 | Ethyl | Tetrahydropyran-3-yl | — | 3.90(m, 2H), 4.23(t, 2H), 7.17–7.43(m, 5H) |
| 4.02 | Propyl | Tetrahydropyran-3-yl | — | 65 |
| 4.03 | Ethyl | Tetrahydropyran-4-yl | — | 3.97(m, 2H), 4.23(t, 2H), 7,17–7.43(m, 5H) |
| 4.04 | Propyl | Tetrahydropyran-4-yl | — | 3.97(m, 2H), 4.23(t, 2H), 7.17–7.43(m, 5H) |
| 4.05 | Ethyl | Tetrahydrothiopyran-3-yl | — | 4.23(t, 2H), 7.17–7.43(m, 5H) |
| 4.06 | Propyl | Tetrahydrothiopyran-3-yl | — | 4.23(t, 2H), 7.17–7.43(m, 5H) |
| 4.07 | Ethyl | Tetrahydropyran-3-yl | 4-F | 3.90(m, 2H), 4.17(t, 2H), 7.00(m, 2H), 7.40(m, 2H) |
| 4.08 | Propyl | Tetrahydropyran-3-yl | 4-F | 3.90(m, 2H), 4.17(t, 2H), 7.00(m, 2H), 7.40(m, 2H) |
| 4.09 | Ethyl | Tetrahydropyran-4-yl | 4-F | 4.00(m, 2H), 4.17(t, 2H), 7.00(m, 2H), 7.40(m, 2H) |
| 4.10 | Propyl | Tetrahydropyran-4-yl | 4-F | 4.00(m, 2H), 4.17(t, 2H), 7.00(m, 2H), 7.40(m, 2H) |
| 4.11 | Ethyl | Tetrahydrothiopyran-3-yl | 4-F | 4.17(t, 2H), 7.00(m, 2H), 7.40(m, 2H), |
| 4.12 | Propyl | Tetrahydrothiopyran-3-yl | 4-F | 4.17(t, 2H), 7.00(m, 2H), 7.40(m, 2H), |
| 4.13 | Ethyl | Tetrahydropyran-3-yl | 4-Cl | 71–75 |
| 4.14 | Propyl | Tetrahydropyran-3-yl | 4-Cl | 63–65 |
| 4.15 | Ethyl | Tetrahydropyran-4-yl | 4-Cl | 4.00(m, 2H), 4.20(t, 2H), 7.30(m, 4H) |
| 4.16 | Propyl | Tetrahydropyran-4-yl | 4-Cl | 4.00(m, 2H), 4.20(t, 2H), 7.30(m, 4H) |
| 4.17 | Ethyl | Tetrahydrothiopyran-3-yl | 4-Cl | 4.20(t, 2H), 7.30(m, 4H) |
| 4.18 | Propyl | Tetrahydrothiopyran-3-yl | 4-Cl | 4.20(t, 2H), 7.30(m, 4H) |
| 4.19 | Ethyl | Tetrahydropyran-3-yl | 2-Cl | 3.90(m, 2H), 4.25(t, 2H), 7.10–7.50(m, 4H) |
| 4.20 | Propyl | Tetrahydropyran-3-yl | 2-Cl | 3.90(m, 2H), 4.25(t, 2H), 7.10–7.50(m, 4H) |
| 4.21 | Ethyl | Tetrahydropyran-4-yl | 2-Cl | 4.00(m, 2H), 4.25(t, 2H), 7.10–7.50(m, 4H) |
| 4.22 | Propyl | Tetrahydropyran-4-yl | 2-Cl | 4.00(m, 2H), 4.25(t, 2H), 7.10–7.50(m, 4H) |
| 4.23 | Ethyl | Tetrahydrothiopyran-3-yl | 2-Cl | 4.25(t, 2H)7.10–7.50(m, 4H) |
| 4.24 | Propyl | Tetrahydrothiopyran-3-yl | 2-Cl | 4.25(t, 2H)7.10–7.50(m, 4H) |
| 4.25 | Ethyl | Tetrahydropyran-3-yl | 2,6-Cl₂ | 3.90(m, 2H)4.20(t, 2H), 7.20(t, 1H) 7.40(d, 2H) |
| 4.26 | Propyl | Tetrahydropyran-3-yl | 2,6-Cl₂ | 3.90(m, 2H)4.20(t, 2H), 7.20(t, 1H) 7.40(d, 2H) |
| 4.27 | Ethyl | Tetrahydropyran-4-yl | 2,6-Cl₂ | 61–64 |
| 4.28 | Propyl | Tetrahydropyran-4-yl | 2,6-Cl₂ | 4.00(m, 2H)4.20(t, 2H), 7.20(t, 1H) 7.40(d, 2H) |
| 4.29 | Ethyl | Tetrahydrothiopyran-3-yl | 2,6-Cl₂ | 4.20(t, 2H) 7.20(t, 2H), 7.40(d, 2H) |
| 4.30 | Propyl | Tetrahydrothiopyran-3-yl | 2,6-Cl₂ | 4.20(t, 2H) 7.20(t, 2H), 7.40(d, 2H) |

TABLE 5

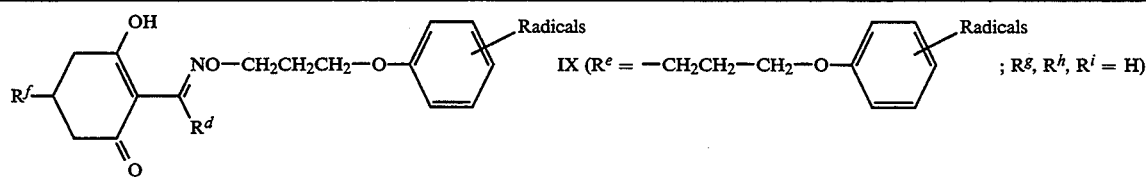

IX ($R^e$ = —CH$_2$CH$_2$—CH$_2$—O—⟨phenyl⟩—Radicals ; $R^g$, $R^h$, $R^i$ = H)

| No. | $R^d$ | $R^f$ | Radicals on phenyl ring | Physical data/$^1$H-NMR [δ in ppm], mp. [°C.] |
|---|---|---|---|---|
| 5.01 | Ethyl | Tetrahydropyran-3-yl | — | 3.90(m, 2H), 4.03(t, 2H), 4.23(t, 2H), 6.90(m, 3H), 7.27(m, 2H) |
| 5.02 | Propyl | Tetrahydropyran-3-yl | — | 3.90(m, 2H), 4.03(t, 2H), 4.23(t, 2H), 6.90(m, 3H), 7.27(m, 2H) |
| 5.03 | Ethyl | Tetrahydropyran-4-yl | — | 3.97(m, 2H), 4.03(t, 2H), 4.23(t, 2H), 6.90(m, 3H), 7.27(m, 2H) |
| 5.04 | Propyl | Tetrahydropyran-4-yl | — | 3.97(m, 2H), 4.03(t, 2H), 4.23(t, 2H), 6.90(m, 3H), 7.27(m, 2H) |
| 5.05 | Ethyl | Tetrahydrothiopyran-3- | — | 4.03(t, 2H), 4.23(t, 2H), 6.90(m, 3H), 7.27(m, 2H) |
| 5.06 | Propyl | Tetrahydrothiopyran-3- | — | 4.03(t, 2H), 4.23(t, 2H), 6.90(m, 3H), 7.27(m, 2H) |
| 5.07 | Ethyl | Tetrahydropyran-3-yl | 2-F | 3.90(m, 2H), 4.10(t, 2H), 4.27(t, 2H), 6.80–7.15(m, 4H) |
| 5.08 | Propyl | Tetrahydropyran-3-yl | 2-F | 3.90(m, 2H), 4.10(t, 2H), 4.27(t, 2H), 6.80–7.15(m, 4H) |
| 5.09 | Ethyl | Tetrahydropyran-4-yl | 2-F | 4.00(m, 2H), 4.10(t, 2H), 4,27(t, 2H), 6.80–7.15(m, 4H) |
| 5.10 | Propyl | Tetrahydropyran-4-yl | 2-F | 76–80 |
| 5.11 | Ethyl | Tetrahydrothiopyran-3-yl | 2-F | 4.10(t, 2H), 4.27(t, 2H), 6.80–7.15(m, 4H), |
| 5.12 | Propyl | Tetrahydrothiopyran-3-yl | 2-F | 4.10(t, 2H), 4.27(t, 2H), 6.80–7.15(m, 4H), |
| 5.13 | Ethyl | Tetrahydropyran-3-yl | 3-F | 3.90(m, 2H), 4.05(t, 2H), 4.27(t, 2H), 6.67(m, 3H), 7.23(m, 1H) |
| 5.14 | Propyl | Tetrahydropyran-3-yl | 3-F | 3.90(m, 2H), 4.05(t, 2H), 4.27(t, 2H), 6.67(m, 3H), 7.23(m, 1H) |
| 5.15 | Ethyl | Tetrahydropyran-4-yl | 3-F | 3.90–4.10(m, 4H), 4,27(t, 2H), 6.67(m, 3H), 7.23(m, 1H) |
| 5.16 | Propyl | Tetrahydropyran-4-yl | 3-F | 3.90–4.10(m, 4H), 4.27(t, 2H), 6.67(m, 3H), 7.23(m, 1H) |
| 5.17 | Ethyl | Tetrahydrothiopyran-3-yl | 3-F | 4.05(t, 2H), 4.27(t, 2H), 6.67(m, 3H) 7.23(m, 1H) |
| 5.18 | Propyl | Tetrahydrothiopyran-3-yl | 3-F | 4.05(t, 2H), 4.27(t, 2H), 6.67(m, 3H) 7.23(m, 1H) |
| 5.19 | Ethyl | Tetrahydropyran-3-yl | 4-F | 3.90(m, 2H), 4.03(t, 2H), 4.27(t, 2H), 6.90(m, 2H), 7.00(m, 2H) |
| 5.20 | Propyl | Tetrahydropyran-3-yl | 4-F | 3.90(m, 2H), 4.03(t, 2H), 4.27(t, 2H), 6.90(m, 2H), 7.00(m, 2H) |
| 5.21 | Ethyl | Tetrahydropyran-4-yl | 4-F | 3.90–4.06(m, 4H), 4.23(t, 2H), 6.90(m, 2H), 7.00(m, 2H) |
| 5.22 | Propyl | Tetrahydropyran-4-yl | 4-F | 3.90–4.06(m, 4H), 4.28(t, 2H), 6.90(m, 2H), 7.00(m, 2H) |
| 5.23 | Ethyl | Tetrahydrothiopyran-3-yl | 4-F | 4.03(t, 2H), 4.27(t, 2H), 6.90(m, 2H), 7.00(m, 2H) |
| 5.24 | Propyl | Tetrahydrothiopyran-3-yl | 4-F | 4.03(t, 2H), 4.27(t, 2H), 6.90(m, 2H), 7.00(m, 2H) |
| 5.25 | Ethyl | Tetrahydropyran-3-yl | 2-Cl | |
| 5.26 | Propyl | Tetrahydropyran-3-yl | 2-Cl | |
| 5.27 | Ethyl | Tetrahydropyran-4-yl | 2-Cl | |
| 5.28 | Propyl | Tetrahydropyran-4-yl | 2-Cl | |
| 5.29 | Ethyl | Tetrahydrothiopyran-3-yl | 2-Cl | |
| 5.30 | Propyl | Tetrahydrothiopyran-3-yl | 2-Cl | |
| 5.31 | Ethyl | Tetrahydropyran-3-yl | 3-Cl | 3.90(m, 2H), 4.06(t, 2H), 4.27(t, 2H), 6.77(m, 1H), 6.90(m, 2H), 7.17(m, 1H) |
| 5.32 | Propyl | Tetrahydropyran-3-yl | 3-Cl | 3.90(m, 2H), 4.06(t, 2H), 4.27(t, 2H), 6.77(m, 1H), 6.90(m, 2H), 7.17(m, 1H) |
| 5.33 | Ethyl | Tetrahydropyran-4-yl | 3-Cl | 3.90–4.10(m, 4H), 4.27(t, 2H), 6.77(m, 1H), 6.90(m, 2H), 7.17(m, 1H) |
| 5.34 | Propyl | Tetrahydropyran-4-yl | 3-Cl | 3.90–4.10(m, 4H), 4.27(t, 2H), 6.77(m, 1H), 6.90(m, 2H), 7.17(m, 1H) |
| 5.35 | Ethyl | Tetrahydrothiopyran-3-yl | 3-Cl* | 4.06(t, 2H), 4.27(t, 2H), 6.77(m, 1H), 6.90(m, 2H), 7.17(m, 1H) |
| 5.36 | Propyl | Tetrahydrothiopyran-3-yl | 3-Cl | 4.06(t, 2H), 4.27(t, 2H), 6.77(m, 1H), 6.90(m, 2H), 7.17(m, 1H) |
| 5.37 | Ethyl | Tetrahydropyran-3-yl | 4-Cl | 3.90(m, 2H), 4.03(t, 2H), 4.23(t, 2H), 6.80(m, 2H), 7.20(m, 2H) |
| 5.38 | Propyl | Tetrahydropyran-3-yl | 4-Cl | 3.90(m, 2H), 4.03(t, 2H), 4.23(t, 2H), 6.80(m, 2H), 7.20(m, 2H) |
| 5.39 | Ethyl | Tetrahydropyran-4-yl | 4-Cl | 3.90–4.09(m, 4H), 4.23(t, 2H), 6.80(m, 2H), 7.20(m, 2H) |
| 5.40 | Propyl | Tetrahydropyran-4-yl | 4-Cl | 3.90–4.09(m, 4H), 4.23(t, 2H), 6.80(m, 2H), 7.20(m, 2H) |

TABLE 5-continued

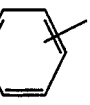

IX ($R^e$ = —CH₂CH₂—CH₂—O—C₆H₄—Radicals ; $R^g$, $R^h$, $R^i$ = H)

| No. | $R^d$ | $R^f$ | Radicals on phenyl ring | Physical data/¹H-NMR [δ in ppm], mp. [°C.] |
|---|---|---|---|---|
| 5.41 | Ethyl | Tetrahydrothiopyran-3-yl | 4-Cl | 4.03(t, 2H), 4.23(t, 2H), 6.80(m, 2H), 7.20(m, 2H) |
| 5.42 | Propyl | Tetrahydrothiopyran-3-yl | 4-Cl | 4.03(t, 2H), 4.23(t, 2H), 6.80(m, 2H), 7.20(m, 2H) |
| 5.43 | Ethyl | Tetrahydropyran-3-yl | 4-NO₂ | 3.90(m, 2H), 4.20(t, 2H), 4.28(t, 2H), 6.93(d, 2H), 8.20(d, H) |
| 5.44 | Propyl | Tetrahydropyran-3-yl | 4-NO₂ | 3.90(m, 2H), 4.20(t, 2H), 4.28(t, 2H), 6.93(d, 2H), 8.20(d, 2H) |
| 5.45 | Ethyl | Tetrahydropyran-4-yl | 4-NO₂ | 4.00(m, 2H), 4.20(t, 2H), 4.28(t, 2H), 6.93(d, 2H), 8.20(d, 2H) |
| 5.46 | Propyl | Tetrahydropyran-4-yl | 4-NO₂ | 4.00(m, 2H), 4.20(t, 2H), 4.28(t, 2H), 6.93(d, 2H), 8,20(d, 2H) |
| 5.47 | Ethyl | Tetrahydrothiopyran-3-yl | 4-NO₂ | 4.20(t, 2H), 4.28(t, 2H), 6.93(d, 2H), 8.20(d, 2H) |
| 5.48 | Propyl | Tetrahydrothiopyran-3-yl | 4-NO₂ | 4.20(t, 2H), 4.28(t, 2H), 6.93(d, 2H), 8.20(d, 2H) |
| 5.49 | Ethyl | Tetrahydropyran-3-yl | 4-Br | 3.90(m, 2H), 4.00 (t, 2H), 4.27(t, 2H), 6.80(d, 2H), 7.37(d, 2H) |
| 5.50 | Propyl | Tetrahydropyran-3-yl | 4-Br | 3.90(m, 2H), 4.00(t, 2H), 4.27(t, 2H), 6.80(d, 2H), 7.37 (d, 2H) |
| 5.51 | Ethyl | Tetrahydropyran-4-yl | 4-Br | 3.90–4.10(m, 4H), 4.27(t, 2H), 6.80(d, 2H), 7.37(d, 2H) |
| 5.52 | Propyl | Tetrahydropyran-4-yl | 4-Br | 3.90–4.10(m, 4H), 4,27(t, 2H), 6.80(d, 2H), 7.37(d, 2H) |
| 5.53 | Ethyl | Tetrahydrothiopyran-4-yl | 4-Br | 4.00(t, 2H), 4.27(t, 2H), 6.80(d, 2H), 7.37(d, 2H) |
| 5.54 | Propyl | Tetrahydrothiopyran-4-yl | 4-Br | 4.00(t, 2H); 4.27(t, 2H), 6.80(d, 2H), 7.37(d, 2H) |

TABLE 6

IX ($R^e$ = —CH₂CH₂CH₂—S—C₆H₄—Radicals ; $R^g$, $R^h$, $R^i$ = H)

| No. | $R^d$ | $R^f$ | Radicals on phenyl ring | Physical data/¹H-NMR [δ in ppm], mp. [°C.] |
|---|---|---|---|---|
| 6.01 | Ethyl | Tetrahydropyran-3-yl | — | 3.90(m, 2H), 4.17(t, 2H), 7.10–7.40(m, 5H) |
| 6.02 | Propyl | Tetrahydropyran-3-yl | — | 3.90(m, 2H), 4.17(t, 2H), 7.10–7.40(m, 5H) |
| 6.03 | Ethyl | Tetrahydropyran-4-yl | — | 4.00(m, 2H), 4.17(t, 2H), 7.10–7.40(m, 5H) |
| 6.04 | Propyl | Tetrahydropyran-4-yl | — | 4.00(m, 2H), 4.17(t, 2H), 7.10–7.40(m, 5H) |
| 6.05 | Ethyl | Tetrahydrothiopyran-3-yl | — | 4.17(t, 2H), 7.10–7.40(m, 5H) |
| 6.06 | Propyl | Tetrahydrothiopyran-3-yl | — | 4.17(t, 2H), 7.10–7.40(m, 5H) |
| 6.07 | Ethyl | Tetrahydropyran-3-yl | 4-F | 3.90(m, 2H), 4.17(t, 2H), 7.00(t, 2H), 7.33(m, 2H) |
| 6.08 | Propyl | Tetrahydropyran-3-yl | 4-F | 3.90(m, 2H), 4.17(t, 2H), 7.00(t, 2H), 7.33(m, 2H) |
| 6.09 | Ethyl | Tetrahydropyran-4-yl | 4-F | 4.00(m, 2H), 4.17(t, 2H), 7.00(t, 2H), 7.33(m, 2H) |
| 6.10 | Propyl | Tetrahydropyran-4-yl | 4-F | 4.00(m, 2H), 4.17(t, 2H), 7.00(t, 2H), 7.33(m, 2H) |
| 6.11 | Ethyl | Tetrahydrothiopyran-3-yl | 4-F | 4.17(t, 2H), 7.00(t, 2H), 7.33(m, 2H) |
| 6.12 | Propyl | Tetrahydrothiopyran-3-yl | 4-F | 4.17(t, 2H), 7.00(t, 2H), 7.33(m, 2H) |
| 6.13 | Ethyl | Tetrahydropyran-3-yl | 4-Cl | 3.90(m, 2H), 4.17(t, 2H), 7.27(s, 4H) |
| 6.14 | Propyl | Tetrahydropyran-3-yl | 4-Cl | 3.90(m, 2H), 4.17(t, 2H), 7.27(s, 4H) |
| 6.15 | Ethyl | Tetrahydropyran-4-yl | 4-Cl | 4.00(m, 2H), 4.17(t, 2H), 7.27(s, 4H) |
| 6.16 | Propyl | Tetrahydropyran-4-yl | 4-Cl | 4.00(m, 2H), 4.17(t, 2H), 7.27(s, 4H) |
| 6.17 | Ethyl | Tetrahydrothiopyran-3-yl | 4-Cl | 4.17(t, 2H), 7.27(s, 4H) |
| 6.18 | Propyl | Tetrahydrothiopyran-3-yl | 4-Cl | 4.17(t, 2H), 7.27(s, 4H) |
| 6.19 | Ethyl | Tetrahydropyran-3-yl | 2-Cl | 3.90(m, 2H), 4.20(t, 2H), 7.07–7.40(m, 4H) |
| 6.20 | Propyl | Tetrahydropyran-3-yl | 2-Cl | 3.90(m, 2H), 4.20(t, 2H), 7.07–7.40(m, 4H) |
| 6.21 | Ethyl | Tetrahydropyran-4-yl | 2-Cl | 4.00(m, 2H), 4.20(t, 2H), 7.07–7.40(m, 4H) |
| 6.22 | Propyl | Tetrahydropyran-4-yl | 2-Cl | 4.00(m, 2H), 4.20(t, 2H), 7.07–7.40(m, 4H) |
| 6.23 | Ethyl | Tetrahydrothiopyran-3-yl | 2-Cl | 4.20(t, 2H), 7.07–7.40(m, 4H) |

TABLE 6-continued

Structure: IX ($R^e$ = —CH$_2$CH$_2$CH$_2$—S—phenyl with Radicals); $R^g$, $R^h$, $R^i$ = H

| No. | $R^d$ | $R^f$ | Radicals on phenyl ring | Physical data/$^1$H-NMR [δ in ppm], mp. [°C.] |
|---|---|---|---|---|
| 6.24 | Propyl | Tetrahydrothiopyran-3-yl | 2-Cl | 4.20(t, 2H), 7.07–7.40(m, 4H) |
| 6.25 | Ethyl | Tetrahydropyran-3-yl | 3-Cl | 3.90(m, 2H), 4.20(t, 2H), 7.17(m, 3H) 7.30(m, 1H) |
| 6.26 | Propyl | Tetrahydropyran-3-yl | 3-Cl | 3.90(m, 2H), 4.20(t, 2H), 7.17(m, 3H) 7.30(m, 1H) |
| 6.27 | Ethyl | Tetrahydropyran-4-yl | 3-Cl | 4.00(m, 2H), 4.20(t, 2H), 7.17(m, 3H) 7.30(m, 1H) |
| 6.28 | Propyl | Tetrahydropyran-4-yl | 3-Cl | 4.00(m, 2H), 4.20(t, 2H), 7.17(m, 3H) 7.30(m, 1H) |
| 6.29 | Ethyl | Tetrahydrothiopyran-3-yl | 3-Cl | 4.20(t, 2H), 7.17(m, 3H), 7.30(m, 1H) |
| 6.30 | Propyl | Tetrahydrothiopyran-3-yl | 3-Cl | 4.20(t, 2H), 7.17(m, 3H), 7.30(m, 1H) |
| 6.31 | Ethyl | Tetrahydropyran-3-yl | 2,5-Cl$_2$ | 3.90(m, 2H), 4.20(t, 2H), 7.07(dd, 1H), 7.20(d, 1H)7.30(d, 1H) |
| 6.32 | Propyl | Tetrahydropyran-3-yl | 2,5-Cl$_2$ | 3.90(m, 2H), 4.20(t, 2H), 7.07(dd, 1H), 7.20(d, 1H)7.30(d, 1H) |
| 6.33 | Ethyl | Tetrahydropyran-4-yl | 2,5-Cl$_2$ | 4.00(m, 2H), 4.20(t, 2H), 7.07(dd, 1H), 7.20(d, 1H)7.30(d, 1H) |
| 6.34 | Propyl | Tetrahydropyran-4-yl | 2,5-Cl$_2$ | 4.00(m, 2H), 4.20(t, 2H), 7.07(dd, 1H), 7.20(d, 1H)7.30(d, 1H) |
| 6.35 | Ethyl | Tetrahydrothiopyran-3-yl | 2,5-Cl$_2$ | 4.20(t, 2H), 7.07(dd, 1H), 7.20(d, 1H) 7.30(d, 1H) |
| 6.36 | Propyl | Tetrahydrothiopyran-3-yl | 2,5-Cl$_2$ | 4.20(t, 2H), 7.07(dd, 1H), 7.20(d, 1H) 7.30(d, 1H) |
| 6.37 | Ethyl | Tetrahydropyran-3-yl | 2,6-Cl$_2$ | 3.90(m, 2H), 4.20(t, 2H), 7.20(t, 1H) 7.40(d, 2H) |
| 6.38 | Propyl | Tetrahydropyran-3-yl | 2,6-Cl$_2$ | 3.90(m, 2H), 4.20(t, 2H), 7.20(t, 1H) 7.40(d, 2H) |
| 6.39 | Ethyl | Tetrahydropyran-4-yl | 2,6-Cl$_2$ | 4.00(m, 2H), 4.20(t, 2H), 7.20(t, 1H) 7.40(d, 2H) |
| 6.40 | Propyl | Tetrahydropyran-4-yl | 2,6-Cl$_2$ | 4.00(m, 2H), 4.20(t, 2H), 7.20(t, 1H) 7.40(d, 2H) |
| 6.41 | Ethyl | Tetrahydrothiopyran-3-yl | 2,6-Cl$_2$ | 4.20(t, 2H), 7.20(t, 1H), 7.40(d, 2H) |
| 6.42 | Propyl | Tetrahydrothiopyran-3-yl | 2,6-Cl$_2$ | 4.20(t, 2H), 7.20(t, 1H), 7.40(d, 2H) |

TABLE 7

Structure: IX ($R^e$ = —CH$_2$CH$_2$—O—CH$_2$—phenyl with Radicals); $R^g$, $R^h$, $R^i$ = H

| No. | $R^d$ | $R^f$ | Radicals on phenyl ring | Physical data/$^1$H-NMR [δ in ppm], mp. [°C.] |
|---|---|---|---|---|
| 7.01 | Ethyl | Tetrahydropyran-3-yl | — | 3.90(m, 2H), 4.25(t, 2H), 4.58(s, 2H), 7.38(s, 5H) |
| 7.02 | Propyl | Tetrahydropyran-3-yl | — | 3.90(m, 2H), 4.25(t, 2H), 4.58(s, 2H), 7.38(s, 5H) |
| 7.03 | Ethyl | Tetrahydropyran-4-yl | — | 4.03(m, 2H), 4.33(m, 2H), 4.60(s, 2H), 7.40(s, 5H) |
| 7.04 | Propyl | Yetrahydropyran-4-yl | — | 4.03(m, 2H), 4.33(m, 2H), 4.60(s, 2H), 7.40(s, 5H) |
| 7.05 | Ethyl | Tetrahydrothiopyran-3-yl | — | 4.27(m, 2H), 4.57(s, 2H), 7.35(s, 5H) |
| 7.06 | Propyl | Tetrahydrothiopyran-3-yl | — | 4.27(m, 2H), 4.57(s, 2H), 7.35(s, 5H) |
| 7.07 | Ethyl | Tetrahydropyran-3-yl | 2-F | 3.93(m, 2H), 4.27(m, 2H), 4.67(s, 2H), 6.93–7.50(m, 4H) |
| 7.08 | Propyl | Tetrahydropyran-3-yl | 2-F | 3.93(m, 2H), 4.27(m, 2H), 4.67(s, 2H), 6.93–7.50(m, 4H) |
| 7.09 | Ethyl | Tetrahydropyran-4-yl | 2-F | 4.03(m, 2H), 4.27(m, 2H), 4.63(s, 2H), 6.97–7.50(m, 4H) |
| 7.10 | Propyl | Tetrahydropyran-4-yl | 2-F | 4.03(m, 2H), 4.27(m, 2H), 4.63(s, 2H), 6.97–7.50(m, 4H) |
| 7.11 | Ethyl | Tetrahydrothiopyran-3-yl | 2-F | 4.27(m, 2H), 4.67(s, 2H), 6.97–7.50(m, 4H) |
| 7.12 | Propyl | Tetrahydrothiopyran-3-yl | 2-F | 4.27(m, 2H), 4.67(s, 2H), 6.97–7.50(m, 4H) |

TABLE 7-continued

Structure: cyclohexane-dione with OH, R^f, R^d substituents, N-O-CH2CH2OCH2-O-phenyl with Radicals; IX (R^e = —CH2CH2—O—CH2—phenyl with Radicals; R^g, R^h, R^i = H)

| No. | R^d | R^f | Radicals on phenyl ring | Physical data/¹H-NMR [δ in ppm], mp. [°C.] |
|---|---|---|---|---|
| 7.13 | Ethyl | Tetrahydropyran-3-yl | 3-F | 3.93(m, 2H), 4.27(m, 2H), 4.57(s, 2H), 6.90–7.15(m, 3H), 7.23–7.40(m, 1H) |
| 7.14 | Propyl | Tetrahydropyran-3-yl | 3-F | 3.93(m, 2H), 4.27(m, 2H), 4.57(s, 2H), 6.90–7.15(m, 3H), 7.23–7.40(m, 1H) |
| 7.15 | Ethyl | Tetrahydropyran-4-yl | 3-F | 4.03(m, 2H), 4.25(m, 2H), 4.60(s, 2H), 6.90–7.18(m, 3H), 7.26–7.40(m, 1H) |
| 7.16 | Propyl | Tetrahydropyran-4-yl | 3-F | 4.03(m, 2H), 4.25(m, 2H), 4.60(s, 2H), 6.90–7.18(m, 3H), 7.26–7.40(m, 1H) |
| 7.17 | Ethyl | Tetrahydrothiopyran-3-yl | 3-F | 4.27(m, 2H), 4.60(s, 2H), 6.90–7.15(m, 3H), 7.23–7.40(m, 1H) |
| 7.18 | Propyl | Tetrahydrothiopyran-3-yl | 3-F | 4.27(m, 2H), 4.60(s, 2H), 6.90–7.15(m, 3H), 7.23–7.40(m, 1H) |
| 7.19 | Ethyl | Tetrahydropyran-3-yl | 4-F | 3.93(m, 2H), 4.23(m, 2H), 4.53(s, 2H), 7.00(m, 2H), 7.30(m, 2H) |
| 7.20 | Propyl | Tetrahydropyran-3-yl | 4-F | 3.93(m, 2H), 4.23(m, 2H), 4.53(s, 2H), 7.00(m, 2H), 7.30(m, 2H) |
| 7.21 | Ethyl | Tetrahydropyran-4-yl | 4-F | 92 |
| 7.22 | Propyl | Tetrahydropyran-4-yl | 4-F | 4.00(m, 2H), 4.23(m, 2H), 4.53(s, 2H), 7.03(m, 2H), 7.30(m, 2H) |
| 7.23 | Ethyl | Tetrahydrothiopyran-3-yl | 4-F | 4.27(m, 2H), 4.53(s, 2H), 7.03(m, 2H), 7.30(m, 2H) |
| 7.24 | Propyl | Tetrahydrothiopyran-3-yl | 4-F | 4.27(m, 2H), 4.53(s, 2H), 7.03(m, 2H), 7.30(m, 2H) |
| 7.25 | Ethyl | Tetrahydropyran-3-yl | 2-Cl | |
| 7.26 | Propyl | Tetrahydropyran-3-yl | 2-Cl | |
| 7.27 | Ethyl | Tetrahydropyran-4-yl | 2-Cl | |
| 7.28 | Propyl | Tetrahydropyrdn-4-yl | 2-Cl | |
| 7.29 | Ethyl | Tetrahydrothiopyran-3-yl | 2-Cl | |
| 7.30 | Propyl | Tetrahydrothiopyran-3-yl | 2-Cl | |
| 7.31 | Ethyl | Tetrahydropyran-3-yl | 3-Cl | |
| 7.32 | Propyl | Tetrahydropyran-3-yl | 3-Cl | |
| 7.33 | Ethyl | Tetrahydropyran-4-yl | 3-Cl | |
| 7.34 | Propyl | Tetrahydropyran-4-yl | 3-Cl | |
| 7.35 | Ethyl | Tetrahydrothiopyran-3-yl | 3-Cl | |
| 7.36 | Propyl | Tetrahydrothiopyran-3-yl | 3-Cl | |
| 7.37 | Ethyl | Tetrahydropyran-3-yl | 4-Cl | 3.93(m, 2H), 4.27(m, 2H), 4.53(s, 2H), 7.28(m, 4H) |
| 7.38 | Propyl | Tetrahydropyran-3-yl | 4-Cl | 3.93(m, 2H), 4.27(m, 2H), 4.53(s, 2H), 7.28(m, 4H) |
| 7.39 | Ethyl | Tetrahydropyran-4-yl | 4-Cl | 67–72 |
| 7.40 | Propyl | Tetrahydropyran-4-yl | 4-Cl | 4.00(m, 2H), 4.23(m, 2H), 4.53(s, 2H), 7.28(m, 4H) |
| 7.41 | Ethyl | Tetrahydrothiopyran-3-yl | 4-Cl | 4.27(m, 2H), 4.53(s, 2H), 7.28(m, 4H) |
| 7.42 | Propyl | Tetrahydrothiopyran-3-yl | 4-Cl | 4.27(m, 2H), 4.53(s, 2H), 7.28(m, 4H) |
| 7.43 | Ethyl | Tetrahydropyran-3-yl | 2-CH₃ | 3.93(m, 2H), 4.23(m, 2H), 4.57(s, 2H), 7.09–7.33(m, 4H) |
| 7.44 | Propyl | Tetrahydropyran-3-yl | 2-CH₃ | 3.93(m, 2H), 4.23(m, 2H), 4.57(s, 2H), 7.09–7.33(m, 4H) |
| 7.45 | Ethyl | Tetrahydropyran-4-yl | 2-CH₃ | 4.00(m, 2H), 4.23(m, 2H), 4.57(s, 2H), 7.09–7.33(m, 4H) |
| 7.46 | Propyl | Tetrahydropyran-4-yl | 2-CH₃ | 4.00(m, 2H), 4.23(m, 2H), 4.57(s, 2H), 7.09–7.33(m, 4H) |
| 7.47 | Ethyl | Tetrahydrothiopyran-3-yl | 2-CH₃ | 4.23(m, 2H), 4.57(s, 2H), 7.09–7.33(m, 4H) |
| 7.48 | Propyl | Tetrahydrothiopyran-3-yl | 2-CH₃ | 4.23(m, 2H), 4.57(s, 2H), 7.09–7.33(m, 4H) |
| 7.49 | Ethyl | Tetrahydropyran-3-yl | 3-CH₃ | 3.93(m, 2H), 4.25(m, 2H), 4.57(s, 2H), 7.00–7.32(m, 4H) |
| 7.50 | Propyl | Tetrahydropyran-3-yl | 3-CH₃ | 3.93(m, 2H), 4.25(m, 2H), 4.57(s, 2H), 7.00–7.32(m, 4H) |
| 7.51 | Ethyl | Tetrahydropyran-4-yl | 3-CH₃ | 4.00(m, 2H), 4.27(m, 2H), 4.57(s, 2H), 7.00–7.32(m, 4H) |
| 7.52 | Propyl | Tetrahydropyran-4-yl | 3-CH₃ | 4.00(m, 2H), 4.27(m, 2H), 4.57(s, 2H), 7.00–7.32(m, 4H) |
| 7.53 | Ethyl | Tetrahydrothiopyran-3-yl | 3-CH₃ | 4.27(m, 2H), 4.60(s, 2H), 7.00–7.32(m, 4H) |
| 7.54 | Propyl | Tetrahydrothiopyran-3-yl | 3-CH₃ | 4.27(m, 2H), 4.60(s, 2H), 7.00–7.32(m, 4H) |
| 7.55 | Ethyl | Tetrahydropyran-3-yl | 4-CH₃ | 3.93(m, 2H), 4.20(m, 2H), 4.53(s, 2H), 7.07–7.30(m, 4H) |
| 7.56 | Propyl | Tetrahydropyran-3-yl | 4-CH₃ | 3.93(m, 2H), 4.20(m, 2H)4.53(s, 2H), |

TABLE 7-continued

Structure: cyclohexenone with OH, R$^f$, R$^d$, =NO—CH$_2$CH$_2$OCH$_2$—phenyl(Radicals); IX (R$^e$ = —CH$_2$CH$_2$—O—CH$_2$—phenyl(Radicals); R$^g$, R$^h$, R$^i$ = H)

| No. | R$^d$ | R$^f$ | Radicals on phenyl ring | Physical data/$^1$H-NMR [δ in ppm], mp. [°C.] |
|---|---|---|---|---|
| 7.57 | Ethyl | Tetrahydropyran-4-yl | 4-CH$_3$ | 7.07–7.30(m, 4H)<br>4.00(m, 2H), 4.23(m, 2H), 4.57(s, 2H),<br>7.03–7.27(m, 4H) |
| 7.58 | Propyl | Tetrahydropyran-4-yl | 4-CH$_3$ | 4.00(m, 2H), 4.23(m, 2H), 4.57(s, 2H),<br>7.03–7.27(m, 4H) |
| 7.59 | Ethyl | Tetrahydrothiopyran-3-yl | 4-CH$_3$ | 4.23(m, 2H), 4.57(s, 2H),<br>7.07–7.30(m, 4H) |
| 7.60 | Propyl | Tetrahydrothiopyran-3-yl | 4-CH$_3$ | 4.28(m, 2H), 4.57(s, 2H),<br>7.07–7.30(m, 4H) |
| 7.61 | Ethyl | Tetrahydropyran-3-yl | 4-tert.-C$_4$H$_9$ | 3.93(m, 2H), 4.23(m, 2H), 4.53(s, 2H),<br>7.20–7.40(m, 4H) |
| 7.62 | Propyl | Tetrahydropyran-3-yl | 4-tert.-C$_4$H$_9$ | 3.93(m, 2H), 4.23(m, 2H), 4.53(s, 2H),<br>7.20–7.40(m, 4H) |
| 7.63 | Ethyl | Tetrahydropyran-4-yl | 4-tert.-C$_4$H$_9$ | 4.00(m, 2H), 4.23(m, 2H), 4.53(s, 2H),<br>7.20–7.40(m, 4H) |
| 7.64 | Propyl | Tetrahydropyran-4-yl | 4-tert.-C$_4$H$_9$ | 4.00(m, 2H), 4.23(m, 2H), 4.53(s, 2H),<br>7.20–7.40(m, 4H) |
| 7.65 | Ethyl | Tetrahydrothiopyran-3-yl | 4-tert.-C$_4$H$_9$ | 4.23(m, 2H), 4.53(s, 2H),<br>7.20–7.40(m, 4H) |
| 7.66 | Propyl | Tetrahydrothiopyran-3-yl | 4-tert.-C$_4$H$_9$ | 4.23(m, 2H), 4.53(s, 2H),<br>7.20–7.40(m, 4H) |

TABLE 8

Structure: cyclohexenone with OH, R$^f$, R$^d$, =NO—CH$_2$CH$_2$SCH$_2$—phenyl(Radicals); IX (R$^e$ = —CH$_2$CH$_2$—S—CH$_2$—phenyl(Radicals); R$^g$, R$^h$, R$^i$ = H)

| No. | R$^d$ | R$^f$ | Radicals on phenyl ring | Physical data/$^1$H-NMR [δ in ppm], mp. [°C.] |
|---|---|---|---|---|
| 8.01 | Ethyl | Tetrahydropyran-3-yl | — | 3.73(s, 2H), 3.90(m, 2H), 4.17(t, 2H),<br>7.28(s, 5H) |
| 8.02 | Propyl | Tetrahydropyran-3-yl | — | 3.73(s, 2H), 3.90(m, 2H), 4.17(t, 2H),<br>7.28(s, 5H) |
| 8.03 | Ethyl | Tetrahydropyran-4-yl | — | 3.77(s, 2H), 4.00(m, 2H), 4.13(t, 2H),<br>7.28(s, 5H) |
| 8.04 | Propyl | Tetrahydropyran-4-yl | — | 3.77(s, 2H), 4.00(m, 2H), 4.13(t, 2H),<br>7.28(s, 5H) |
| 8.05 | Ethyl | Tetrahydrothiopyran-3-yl | — | 3.80(s, 2H), 4.13(t, 2H), 7.28(s, 5H) |
| 8.06 | Propyl | Tetrahydrothiopyran-3-yl | — | 3.80(s, 2H), 4.13(t, 2H), 7.28(s, 5H) |
| 8.07 | Ethyl | Tetrahydropyran-3-yl | 4-F | 3.72(s, 2H), 3.90(m, 2H), 4.13(t, 2H),<br>7.00(m, 2H), 7.30(m, 2H) |
| 8.08 | Propyl | Tetrahydropyran-3-yl | 4-F | 3.72(s, 2H), 3.90(m, 2H), 4.13(t, 2H),<br>7.00(m, 2H), 7.30(m, 2H) |
| 8.09 | Ethyl | Tetrahydropyran-4-yl | 4-F | 63–65 |
| 8.10 | Propyl | Tetrahydropyran-4-yl | 4-F | 3.73(s, 2H), 4.00(m, 2H), 4.13(t, 2H),<br>7.00(m, 2H), 7.30(m, 2H) |
| 8.11 | Ethyl | Tetrahydrothiopyran-3-yl | 4-F | 3.75(s, 2H), 4.13(t, 2H), 7.00(m, 2H),<br>7.30(m, 2H) |
| 8.12 | Propyl | Tetrahydrothiopyran-3-yl | 4-F | 3.75(s, 2H), 4.13(t, 2H), 7.00(m, 2H),<br>7.30(m, 2H) |
| 8.13 | Ethyl | Tetrahydropyran-3-yl | 4-Cl | 3.77(s, 2H), 3.93(m, 2H), 4.13(t, 2H),<br>7.30(s, 4H) |
| 8.14 | Propyl | Tetrahydropyran-3-yl | 4-Cl | 3.77(s, 2H), 3.93(m, 2H), 4.13(t, 2H),<br>7.30(s, 4H) |
| 8.15 | Ethyl | Tetrahydropyran-4-yl | 4-Cl | 3.73(s, 2H), 4.00(m, 2H), 4.17(t, 2H),<br>7.30(s, 4H) |
| 8.16 | Propyl | Tetrahydropyran-4-yl | 4-Cl | 3.73(s, 2H), 4.00(m, 2H), 4.17(t, 2H),<br>7.30(s, 4H) |
| 8.17 | Ethyl | Tetrahydrothiopyran-3-yl | 4-Cl | 3.73(s, 2H), 4.13(m, 2H), 7.30(s, 4H) |
| 8.18 | Propyl | Tetrahydrothiopyran-3-yl | 4-Cl | 3.73(s, 2H), 4.13(m, 2H), 7.30(s, 4H) |

TABLE 9

IX ($R^e$ = —CH₂CH₂CH₂CH₂—O—⟨phenyl⟩—Radicals ; $R^g$, $R^h$, $R^i$ = H)

| No. | $R^d$ | $R^f$ | Radicals on phenyl ring | Physical data/$^1$H-NMR [δ in ppm], mp. [°C.] |
|---|---|---|---|---|
| 9.01 | Ethyl | Tetrahydropyran-3-yl | — | 3.70–4.20(m, 6H), 6.90(m, 3H), 7.30(m, 2H) |
| 9.02 | Propyl | Tetrahydropyran-3-yl | — | 3.70–4.20(m, 6H), 6.90(m, 3H), 7.30(m, 2H) |
| 9.03 | Ethyl | Tetrahydropyran-4-yl | — | 3.83–4.23(m, 6H), 6.90(m, 3H), 7.30(m, 2H) |
| 9.04 | Propyl | Tetrahydropyran-4-yl | — | 3.83–4.23(m, 6H), 6.90(m, 3H), 7.30(m, 2H) |
| 9.05 | Ethyl | Tetrahydrothiopyran-3-yl | — | 4.00(bs, 2H), 4.13(bs, 2H), 6.90(m, 3H) 7.30(m, 2H) |
| 9.06 | Propyl | Tetrahydrothiopyran-3-yl | — | 4.00(bs, 2H), 4.13(bs, 2H), 6.90(m, 3H) 7.30(m, 2H) |
| 9.07 | Ethyl | Tetrahydropyran-3-yl | 2-F | 3.93(m, 2H), 4.00–4.20(m, 4H), 6.80–7.15(m, 4H) |
| 9.08 | Propyl | Tetrahydropyran-3-yl | 2-F | 3.93(m, 2H), 4.00–4.20(m, 4H), 6.80–7.15(m, 4H) |
| 9.09 | Ethyl | Tetrahydropyran-4-yl | 2-F | 68–72 |
| 9.10 | Propyl | Tetrahydropyran-4-yl | 2-F | 3.90–4.20(m, 6H), 6.80–7.15(m, 4H) |
| 9.11 | Ethyl | Tetrahydrothiopyran-3-yl | 2-F | 4.00–4.20(m, 4H), 6.80–7.15(m, 4H) |
| 9.12 | Propyl | Tetrahydrothiopyran-3-yl | 2-F | 4.00–4.20(m, 4H), 6.80–7.15(m, 4H) |
| 9.13 | Ethyl | Tetrahydropyran-3-yl | 3-F | |
| 9.14 | Propyl | Tetrahydropyran-3-yl | 3-F | |
| 9.15 | Ethyl | Tetrahydropyran-4-yl | 3-F | |
| 9.16 | Propyl | Tetrahydropyran-4-yl | 3-F | |
| 9.17 | Ethyl | Tetrahydrothiopyran-3-yl | 3-F | |
| 9.18 | Propyl | Tetrahydrothiopyran-3-yl | 3-F | |
| 9.19 | Ethyl | Tetrahydropyran-3-yl | 4-F | 3.80–4.20(m, 6H), 6.75–7.05(m, 4H) |
| 9.20 | Propyl | Tetrahydropyran-3-yl | 4-F | 3.80–4.20(m, 6H), 6.75–7.05(m, 4H) |
| 9.21 | Ethyl | Tetrahydropyran-4-yl | 4-F | 3.90–4.20(m, 6H), 6.75–7.05(m, 4H) |
| 9.22 | Propyl | Tetrahydropyran-4-yl | 4-F | 3.90–4.20(m, 6H), 6.75–7.05(m, 4H) |
| 9.23 | Ethyl | Tetrahydrothiopyran-3-yl | 4-F | 3.90–4.20(m, 4H), 6.75–7.05(m, 4H) |
| 9.24 | Propyl | Tetrahydrothiopyran-3-yl | 4-F | 3.90–4.20(m, 4H), 6.75–7.05(m, 4H) |
| 9.25 | Ethyl | Tetrahydropyran-3-yl | 4-Cl | 3.80–4.20(m, 6H), 6.80(m, 2H), 7.20(m, 2H) |
| 9.26 | Propyl | Tetrahydropyran-3-yl | 4-Cl | 3.80–4.20(m, 6H), 6.80(m, 2H), 7.20(m, 2H) |
| 9.27 | Ethyl | Tetrahydropyran-4-yl | 4-Cl | 3.90–4.20(m, 6H), 6.80(m, 2H), 7.20(m, 2H) |
| 9.28 | Propyl | Tetrahydropyran-4-yl | 4-Cl | 3.90–4.20(m, 6H), 6.80(m, 2H), 7.20(m, 2H) |
| 9.29 | Ethyl | Tetrahydrothiopyran-3-yl | 4-Cl | 3.90–4.20(m, 4H), 6.80(m, 2H), 7.20(m, 2H) |
| 9.30 | Propyl | Tetrahydrothiopyran-3-yl | 4-Cl | 3.90–4.20(m, 4H), 6.80(m, 2H), 7.20(m, 2H) |
| 9.31 | Ethyl | Tetrahydropyran-3-yl | 2,6-Cl₂ | 3.93(m, 2H), 4.00–4.25(m, 4H), 7.00(t, 1H), 7.30(d, 2H) |
| 9.32 | Propyl | Tetrahydropyran-3-yl | 2,6-Cl₂ | 3.93(m, 2H), 4.00–4.25(m, 4H), 7.00(t, 1H), 7.30(d, 2H) |
| 9.33 | Ethyl | Tetrahydropyran-4-yl | 2,6-Cl₂ | 3.90–4.25(m, 6H), 7.00(t, 1H), 7.30(d, 2H) |
| 9.34 | Propyl | Tetrahydropyran-4-yl | 2,6-Cl₂ | 3.90–4.25(m, 6H), 7.00(t, 1H), 7.30(d, 2H) |
| 9.35 | Ethyl | Tetrahydrothiopyran-3-yl | 2,6-Cl₂ | 4.00–4.20(m, 4H), 7.00(t, 1H), 7.30(d, 2H) |
| 9.36 | Propyl | Tetrahydrothiopyran-3-yl | 2,6-Cl₂ | 4.00–4.20(m, 4H), 7.00(t, 1H), 7.30(d, 2H) |

TABLE 10

IX ($R^e$ = —CH₂CH₂—O—CH₂CH₂—⟨phenyl⟩—Radicals ; $R^g$, $R^h$, $R^i$ = H)

| No. | $R^d$ | $R^f$ | Radicals on phenyl ring | Physical data/$^1$H-NMR [δ in ppm], mp. [°C.] |
|---|---|---|---|---|
| 10.01 | Ethyl | Tetrahydropyran-3-yl | — | 3.90(m, 2H), 4.20(m, 2H), 7.25(m, 5H) |

TABLE 10-continued

IX ($R^e$ = —CH$_2$CH$_2$—O—CH$_2$CH$_2$—⟨phenyl⟩-Radicals ; $R^g$, $R^h$, $R^i$ = H)

| No. | $R^d$ | $R^f$ | Radicals on phenyl ring | Physical data/$^1$H-NMR [δ in ppm], mp. [°C.] |
|---|---|---|---|---|
| 10.02 | Propyl | Tetrahydropyran-3-yl | — | 3.90(m, 2H), 4.20(m, 2H), 7.25(m, 5H) |
| 10.03 | Ethyl | Tetrahydropyran-4-yl | — | |
| 10.04 | Propyl | Tetrahydropyran-4-yl | — | |
| 10.05 | Ethyl | Tetrahydrothiopyran-3-yl | — | 4.20(m, 2H), 7.25(m, 5H) |
| 10.06 | Propyl | Tetrahydrothiopyran-3-yl | — | 4.20(m, 2H), 7.25(m, 5H) |
| 10.07 | Ethyl | Tetrahydropyran-3-yl | 4-F | 3.90(m, 2H), 4.17(m, 2H), 6.93(m, 2H), 7.13(m, 2H) |
| 10.08 | Propyl | Tetrahydropyran-3-yl | 4-F | 3.90(m, 2H), 4.17(m, 2H), 6.93(m, 2H), 7.13(m, 2H) |
| 10.09 | Ethyl | Tetrahydropyran-4-yl | 4-F | |
| 10.10 | Propyl | Tetrahydropyran-4-yl | 4-F | |
| 10.11 | Ethyl | Tetrahydrothiopyran-3-yl | 4-F | 4.17(m, 2H), 6.93(m, 2H), 7.13(m, 2H) |
| 10.12 | Propyl | Tetrahydrothiopyran-3-yl | 4-F | 4.17(m, 2H), 6.93(m, 2H), 7.13(m, 2H) |
| 10.13 | Ethyl | Tetrahydropyran-3-yl | 4-Cl | 3.90(m, 2H), 4.17(m, 2H), 7.13(m, 4H) |
| 10.14 | Propyl | Tetrahydropyran-3-yl | 4-Cl | 3.90(m, 2H), 4.17(m, 2H), 7.13(m, 4H) |
| 10.15 | Ethyl | Tetrahydropyran-4-yl | 4-Cl | |
| 10.16 | Propyl | Tetrahydropyran-4-yl | 4-Cl | |
| 10.17 | Ethyl | Tetrahydrothiopyran-3-yl | 4-Cl | 4.17(m, 2H), 7.13(m, 4H) |
| 10.18 | Propyl | Tetrahydrothiopyran-3-yl | 4-Cl | 4.17(m, 2H), 7.13(m, 4H) |

TABLE 11

IX ($R^e$ = —CH$_2$CH$_2$CH$_2$CH$_2$CH$_2$—O—⟨phenyl⟩-Radicals ; $R^g$, $R^h$, $R^i$ = H)

| No. | $R^d$ | $R^f$ | Radicals on phenyl ring | Physical data/$^1$H-NMR [δ in ppm], mp. [°C.] |
|---|---|---|---|---|
| 11.01 | Ethyl | Tetrahydropyran-3-yl | — | 3.80–4.17(m, 6H), 6.90(m, 3H), 7.27(m, 2H) |
| 11.02 | Propyl | Tetrahydropyran-3-yl | — | 3.80–4.17(m, 6H), 6.90(m, 3H), 7.27(m, 2H) |
| 11.03 | Ethyl | Tetrahydropyran-4-yl | — | 3.90–4.17(m, 6H), 6.90(m, 3H), 7.27(m, 2H) |
| 11.04 | Propyl | Tetrahydropyran-4-yl | — | 3.90–4.17(m, 6H), 6.90(m, 3H), 7.27(m, 2H) |
| 11.05 | Ethyl | Tetrahydrothiopyran-3-yl | — | 3.97(t, 2H), 4.07(t, 2H), 6.90(m, 3H), 7.27(m, 2H) |
| 11.06 | Propyl | Tetrahydrothiopyran-3-yl | — | 3.97(t, 2H), 4.07(t, 2H), 6.90(m, 3H), 7.27(m, 2H) |
| 11.07 | Ethyl | Tetrahydropyran-3-yl | 4-F | 3.90(m, 4H), 4.03(t, 2H), 6.70–7.03(m, 4H) |
| 11.08 | Propyl | Tetrahydropyran-3-yl | 4-F | 3.90(m, 4H), 4.03(t, 2H), 6.70–7.03(m, 4H) |
| 11.09 | Ethyl | Tetrahydropyran-4-yl | 4-F | 3.83–4.13(m, 6H), 6.70–7.03(m, 4H) |
| 11.10 | Propyl | Tetrahydropyran-4-yl | 4-F | 3.83–4.13(m, 6H), 6.70–7.03(m, 4H) |
| 11.11 | Ethyl | Tetrahydrothiopyran-3-yl | 4-F | 3.90(t, 2H), 4.03(t, 2H)6.70–7.03(m, 4H) |
| 11.12 | Propyl | Tetrahydrothiopyran-3-yl | 4-F | 3.90(t, 2H), 4.03(t, 2H)6.70–7.03(m, 4H) |
| 11.13 | Ethyl | Tetrahydropyran-3-yl | 4-Cl | 3.80–4.10(m, 6H), 6.80(d, 2H), 7.20(d, 2H) |
| 11.14 | Propyl | Tetrahydropyran-3-yl | 4-Cl | 3.80–4.10(m, 6H), 6.80(d, 2H), 7.20(d, 2H) |
| 11.15 | Ethyl | Tetrahydropyran-4-yl | 4-Cl | 3.87–4.10(m, 6H), 6.80(d, 2H), 7.20(d, 2H) |
| 11.16 | Propyl | Tetrahydropyran-4-yl | 4-Cl | 3.87–4.10(m, 6H), 6.80(d, 2H), 7.20(d, 2H) |
| 11.17 | Ethyl | Tetrahydrothiopyran-3-yl | 4-Cl | 54–61 |
| 11.18 | Propyl | Tetrahydrothiopyran-3-yl | 4-Cl | 3.90(t, 2H), 4.07(t, 2H), 6.80(d, 2H) 7.20(d, 2H) |

TABLE 12

$$\text{IX}$$

Structure: cyclohexenone with $OR^i$, $=NOR^e$ attached to $R^d$ group, $R^f$, $R^g$, $R^h$ substituents.

| No. | $R^d$ | $R^e$ | $R^f$ | $R^g$ | $R^h$ | $R^i$ | Reference |
|---|---|---|---|---|---|---|---|
| 12.1 | $C_3H_7$ | $CH_2CH=CH_2$ | $CH_3$ | $CH_3$ | $CO_2CH_3$ | Na | DE-A 2 439 104 |
| 12.2 | $C_3H_7$ | $CH_2CH_3$ | $CH_2CH(CH_3)SCH_2CH_3$ | H | H | H | DE-A 2 822 304 |
| 12.3 | $C_2H_5$ | $CH_2CH=CHCl$ | $CH_2CH(CH_3)SCH_2CH_3$ | H | H | H | US-A 4 440 566 |
| 12.4 | $C_3H_7$ | $CH_2CH=CHCl$ | $CH_2CH(CH_3)SCH_2CH_3$ | H | H | H | US-A 4 440 566 |
| 12.5 | $C_3H_7$ | $C_2H_5$ | 3-methyl-thian | H | H | H | EP-A 71 707 |
| 12.6 | $C_2H_5$ | $C_2H_5$ | 3-methyl-thian | H | H | H | EP-A 71 707 |
| 12.7 | $CH_3$ | $CH_2CH=CHCH_3$ | 3-methyl-thian | H | H | H | EP-A 71 707 |
| 12.8 | $C_3H_7$ | $C_2H_5$ | 3-methyl-tetrahydropyran | H | H | H | EP-A 71 707 |
| 12.9 | $C_2H_5$ | $CH_2CH=CHCl$ | 4-methyl-tetrahydropyran | H | H | H | EP-A 142 741 |
| 12.10 | $C_3H_7$ | $C_2H_5$ | 3-methyl-pyridine | H | H | H | EP-A 66 195 |

TABLE 12-continued

IX: structure with OR^i, NOR^e, R^d, R^f, R^g, R^h on cyclohexenone ring

| No. | R^d | R^e | R^f | R^g | R^h | R^i | Reference |
|---|---|---|---|---|---|---|---|
| 12.11 | C₂H₅ | C₂H₅ | 4-methylphenyl | H | H | H | DE-A 24 39 104 |
| 12.12 | C₂H₅ | CH₂CH=CHCH₃ | 4-ethylphenyl | H | H | H | DE-A 38 08 072 |
| 12.13 | C₂H₅ | C₂H₅ | 2,4,6-trimethylphenyl | H | H | H | EP-A 880 301 |
| 12.14 | C₃H₇ | CH₂CH=CHCl | 4-methylcyclohexyl | H | H | H | EP-A 88 299 |
| 12.15 | C₃H₇ | CH₂CH=CHCH₃ | 4-methylcyclohexyl | H | H | H | EP-A 88 299 |
| 12.16 | C₂H₅ | CH₂CH=CHCH₃ | 3-isopropyl-isoxazol-5-yl (CH(CH₃)₂ substituted isoxazole) | H | H | H | EP-A 238 021 |

TABLE 12-continued

IX

| No. | $R^d$ | $R^e$ | $R^f$ | $R^g$ | $R^h$ | $R^i$ | Reference |
|---|---|---|---|---|---|---|---|
| 12.17 | $C_3H_7$ | $CH_2CH=CHCH_3$ | CH(CH$_3$)$_2$ isoxazole | H | H | H | EP-A 238 021 |
| 12.18 | $C_2H_5$ | $CH_2CH=CHCl$ | $OCH_2-C\equiv CH$ substituted phenyl | H | H | H | EP-A 137 174 |
| 12.19 | $C_3H_7$ | $C_2H_5$ | $CH_2OC_2H_5$ substituted phenyl | H | H | H | EP-A 2 137 200 |
| 12.20 | $C_3H_7$ | $C_2H_5$ | dibromo-tetrahydropyran | H | H | H | EP-A 230 235 |
| 12.21 | $C_3H_7$ | $CH_2CH=CHCl$ | dibromo-tetrahydropyran | H | H | H | EP-A 230 235 |
| 12.22 | $C_3H_7$ | $CH_2CH=CHCl$ | trimethylcyclohexenyl | | | | EP-A 46 860 |

TABLE 12-continued

Structure IX:

$$\text{structure with } OR^i, NOR^e, R^d, R^f, R^g, R^h, \text{ and } =O$$

| No. | $R^d$ | $R^e$ | $R^f$ | $R^g$ | $R^h$ | $R^i$ | Reference |
|---|---|---|---|---|---|---|---|
| 12.23 | $C_3H_7$ | $C_2H_5$ | cyclohexyl | H | H | H | JP-A 540 191 945 |
| 12.24 | $C_3H_7$ | $C_2H_5$ | cyclohexenyl | H | H | H | EP-A 46 860 |
| 12.25 | $CH_3$ | $CH_2CH=CHCl$ | 4-methylcyclohexyl | H | H | H | EP-A 88 299 |
| 12.26 | $C_3H_7$ | $C_2H_5$ | 4-CF$_3$-phenyl | H | H | K | EP-A 137 174 |
| 12.27 | $C_2H_5$ | $CH_2CH=CHCl$ | 2,6,6-trimethylcyclohexenyl | H | H | H | EP-A 46 860 |
| 12.28 | $C_3H_7$ | $CH_2CH=CHCH_3$ | 2-methylthiazolyl | H | H | H | EP-A 125 094 |

TABLE 12-continued

| No. | R$^d$ | R$^e$ | R$^f$ | R$^g$ | R$^h$ | R$^i$ | Reference |
|---|---|---|---|---|---|---|---|
| 12.29 | C$_3$H$_7$ | CH$_2$CH=CHCl | (5-methyl-thiazol-2-yl) | H | H | H | EP-A 125 094 |
| 12.30 | C$_3$H$_7$ | C$_2$H$_5$ | 2,4,6-trimethylcyclohexyl | H | H | H | EP-A 88 299 |
| 12.31 | C$_3$H$_7$ | CH$_2$CH=CH$_2$ | 1-hydroxy-1-methyl-3-(ethylthio)-5-methylcyclohexyl | H | H | H | EP-A 228 598 |
| 12.32 | C$_2$H$_5$ | C$_2$H$_5$ | 2-hydroxy-4-methylcyclohexyl | H | H | H | EP-A 228 598 |
| 12.33 | C$_3$H$_7$ | C$_2$H$_5$ | (1-methylpyrazol-3-yl) | H | H | H | EP-A 66 195 |

TABLE 12-continued

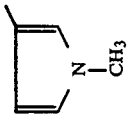

IX

| No. | $R^d$ | $R^e$ | $R^f$ | $R^g$ | $R^h$ | $R^i$ | Reference |
|---|---|---|---|---|---|---|---|
| 12.34 | $C_3H_7$ | $CH_2CH=CHCl$ | ![pyrrole-NCH3] | H | H | H | EP-A 66195 |
| 12.35 | $C_3H_7$ | $CH_2CH=CH_2$ | ![thiazole-CH3] | H | H | H | EP-A 125 094 |
| 12.36 | $C_3H_7$ | $C_3H_7$ | $CH(SCH_2CH_3)_2$ | H | H | H | EP-A 230 260 |
| 12.37 | $C_3H_7$ | $C_2H_5$ | ![methyl-thiane-S=O] | H | H | H | EP-A 115 808 |
| 12.38 | $C_3H_7$ | $C_2H_5$ | ![methyl-thiane-SO2] | H | H | H | EP-A 115 808 |
| 12.39 | $C_3H_7$ | $C_2H_5$ | $CH_3$ | $CH_3$ | $C(CH_3)=NOCH_3$ | H | EP-A 172 551 |
| 12.40 | $C_3H_7$ | $CH_2CH=CH_2$ | ![methyl-thiane-SO2] | OH | H | H | Proceedings Brit. Crop-Protection Conference -weeds 1985 Vol. 1 pages 93–98 |

TABLE 12-continued

Structure IX:

$$\text{structure with } OR^i, NOR^e, R^d, R^f, R^g, R^h \text{ substituents on cyclohexenone}$$

| No. | $R^d$ | $R^e$ | $R^f$ | $R^g$ | $R^h$ | $R^i$ | Reference |
|-----|-------|-------|-------|-------|-------|-------|-----------|
| 12.41 | $C_2H_5$ | CH$_2$CH=CH—CH$_2$— (4-Cl-phenyl) | 3-methyl-tetrahydrothiopyran | H | H | H | EP-A 38 38 309 |
| 12.42 | $C_2H_5$ | CH$_2$CH$_2$—CH=CH— (4-Cl-phenyl) | 3-methyl-tetrahydrothiopyran | H | H | H | EP-A 38 38 309 |
| 12.43 | $C_2H_5$ | CH$_2$CH$_2$—CH=CH— (4-F-phenyl) | 3-methyl-tetrahydrothiopyran | H | H | H | EP-A 38 38 309 |
| 12.44 | n-$C_3H_7$ | CH$_2$CH$_2$—CH=CH— (4-F-phenyl) | 3-methyl-tetrahydrothiopyran | H | H | H | EP-A 38 38 309 |
| 12.45 | $C_2H_5$ | CH$_2$CH=CH—CH$_2$— (phenyl) | 3-methyl-tetrahydrothiopyran | H | H | H | EP-A 38 38 309 |
| 12.46 | n-$C_3H_7$ | CH$_2$-(5-Cl-thiophen-2-yl) | 3-methyl-tetrahydrothiopyran | H | H | H | EP-A 177 913 |
| 12.47 | $C_2H_5$ | CH$_2$-(5-Cl-thiophen-2-yl) | 3-methyl-tetrahydrothiopyran | H | H | H | EP-A 177 913 |

TABLE 12-continued
Structure IX:
| No. | $R^d$ | $R^e$ | $R^f$ | $R^g$ | $R^h$ | $R^i$ | Reference |
|---|---|---|---|---|---|---|---|
| 12.48 | $C_2H_5$ | 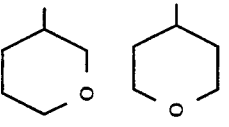 | 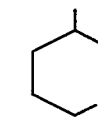 | H | H | H | EP-A 177 913 |
| 12.49 | $n\text{-}C_3H_7$ |  |  | H | H | H | EP-A 177 913 |
| 12.50 | $n\text{-}C_3H_7$ | 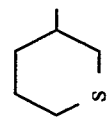 | 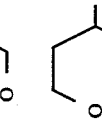 | H | H | H | EP-A 177 913 |
| 12.51 | $CH_3$ |  | 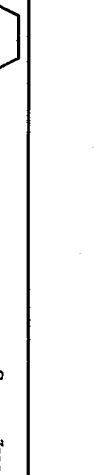 | H | H | H | EP-A 177 913 |
| 12.52 | $C_2H_5$ | 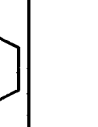 | 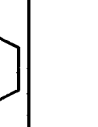 | H | H | H | EP-A 177 913 |

TABLE 13
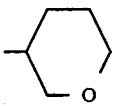
IX (R$^e$ = —CH$_2$(CH$_2$)$_2$CH$_2$— 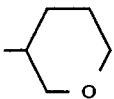 ; R$^g$, R$^h$, R$^i$ = H)
| No. | R$^d$ | R$^f$ | Radicals on phenyl ring | Physical data [NMR* (δ in ppm)] |
|---|---|---|---|---|
| 13.01 | C$_2$H$_5$ | 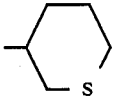 | 4-F | 2.9(broad, 2H); 4.1(broad, 2H) |
| 13.02 | n-C$_3$H$_7$ | 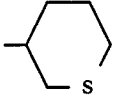 | 4-F | 2.9(t, 2H); 4.05(broad, 2H) |
| 13.03 | C$_2$H$_5$ | 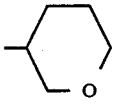 | 4-F | 2.9(t, 2H); 4.05(broad, 2H) |
| 13.04 | n-C$_3$H$_7$ | 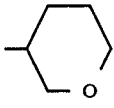 | 4-F | 2.9(t, 2H); 4.05(broad, 2H) |
| 13.05 | C$_2$H$_5$ | 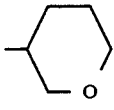 | 4-F | 4.05(broad, 2H) |
| 13.06 | n-C$_3$H$_7$ | 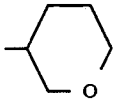 | 4-F | 4.05(broad, 2H) |
| 13.07 | C$_2$H$_5$ | | 4-Cl | 2.9(t, 2H); 4.05(broad, 2H) |
| 13.08 | n-C$_3$H$_7$ | 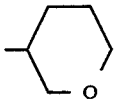 | 4-Cl | 2.9(t, 2H); 4.05(broad, 2H) |
| 13.09 | C$_2$H$_5$ | | 4-Cl | 2.9(t, 2H); 4.05(broad, 2H) |
| 13.10 | n-C$_3$H$_7$ | 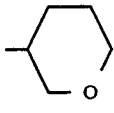 | 4-Cl | 2.9(breit, 2H); 4.05(broad, 2H) |
| 13.11 | C$_2$H$_5$ | 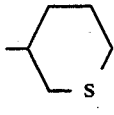 | 4-Cl | 4.05 (broad, 2H) |

TABLE 13-continued

| No. | $R^d$ | $R^f$ | Radicals on phenyl ring | Physical data [NMR* ($\delta$ in ppm)] |
|---|---|---|---|---|
| 13.12 | n-$C_3H_7$ | (tetrahydropyran-yl, S) | 4-Cl | 4.05 (broad, 2H) |

*selected signals

Herbicidal active ingredients and antidote compounds can be applied together or separately, after emergence, to the leaves and shoots of the crops and of the undesirable grasses. The antidote agent is preferably applied simultaneously with the herbicidal active ingredient. Separate application is also possible, the antidote being applied first to the field, followed by the herbicidal active ingredient. The herbicidal active ingredient and antidote may be present as a spray, formulated together or separately in suspendable, emulsifiable or soluble form.

Antidote effects are also achieved by treating the seeds of the crops or the seedlings with the antidote prior to sowing or prior to planting out. The herbicidal active ingredient is then applied alone in the conventional manner.

In the case of seed treatment, in general from 0.1 to 10 g, preferably from 1 to 2 g, of active ingredient are required per kilogram of seed.

In the application of the antidote by means of seed swelling or in the treatment of seedlings, solutions which contain the antagonistic ingredient in a concentration of from 1 to 10,000 ppm, in particular from 100 to 10,000 ppm, are preferably used.

For herbicidal 2-(4-hetaryloxy)- or 2-(4-aryloxy)-phenoxyacetic acid derivatives VIII, different amounts of an antidote compound are required when the herbicide is used in different crops. The ratios can be varied within wide ranges. They are also dependent on the structure of 2-(4-hetaryloxy)- or 2-(4-aryloxy)-phenoxyacetic acid derivatives VIII and on the particular target crop. Suitable weight ratios of herbicidal active ingredients to antidote compound of from 1:10 to 1:0.01, preferably from 1:4 to 1:0.1.

For the same cyclohexenone derivative IX, different amounts of an antidote compound are required when the cyclhexenone derivative IX is used in different crops. The ratios in which the cyclohexenone derivative IX and a 2-amino-4-oxo-4H-benzopyran I or I' are used can be varied within wide ranges. They are dependent on the structure of the cyclohexenone derivative IX and of the 2-amino-4-oxo-4H-benzopyran I or I' and on the particular crop. Suitable weight ratios of herbicidal active ingredient to antidote compound are from 1:10 to 1:0.01, preferably from 1:4 to 1:0.25, both for joint and for separate applications.

The novel agents or, in the case of separate application, the herbicidal active ingredients or the antidotes are applied, for example, in the form of directly sprayable solutions, powders, suspensions, including concentrated aqueous, oily or other suspensions, or dispersion, emulsions, oil dispersions, pastes, dusts, broadcasting agents or granules, by spraying, nebulizing, dusting, broadcasting or pouring. The application forms depend entirely on the intended uses.

For the preparation of directly sprayable solutions, emulsions, pastes and oil dispersions, mineral oil fractions having a medium to high boiling point, such as kerosene or diesel oil, as well as coal tar oils and oils of vegetable or animal origin, aliphatic, cyclic or aromatic hydrocarbons, e.g. benzene, toluene, xylene, paraffin, tetrahydronaphthalene, alkylated naphthalenes or derivatives thereof, for example methanol, ethanol, propanol, butanol, chloroform, carbon tetrachloride, cyclohexanol, cyclohexanone, chlorobenzene or isophorone, and strongly polar solvents, e.g. dimethylformamide, dimethyl sulfoxide, N-methylpyrrolidone and water, are suitable.

Aqueous application forms can be prepared from emulsion concentrates, pastes, wettable powders or oil dispersions by adding water. For the preparation of emulsions, pastes or oil dispersions, the herbicidal active ingredient and/or the antidote, as such or dissolved in an oil or solvent, can be homogenized in water by means of wetting agents, adherents, dispersants or emulsifiers. However, it is also possible to prepare concentrates which consist of herbicidal active ingredient and/or antidote, wetting agents, adherents, dispersants or emulsifiers ad possibly solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol- [sic], octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusts can be prepared by mixing and milling the herbicidal active ingredient and/or the antidote together with a solid carrier.

Granules, for example coated, impregnated and homogeneous granules, can be prepared by binding the active ingredients to solid carriers. Examples of solid carriers are mineral earths, such as silica gel, silicas, silica gels [sic], silicates, talc, kaolin, attaclay, limestone, chalk, talc [sic], bole, loess, clay, dolomite, kieselguhr, calcium sulfate, magnesium sulfate, magnesium oxide, milled plastics, fertilizers, eg. ammonium sulfate, ammonium phosphate, ammonium nitrate and ureas, and vegetable products, such as grain flours, bark meal, wood meal and nutshell meal, cellulosic powders and other solid carriers.

The formulations contain from 0.01 to 95, preferably from 0.5 to 90, % by weight of herbicidal active ingredient and antidote. The application rates of herbicidal active ingredient are from 0.05 to 5 kg/ha active ingredient (a.i.).

In addition to the 2-amino-4-oxo-4H-benzopyran I or I' as an antidote and the herbicide selected from the group consisting of the 2-(4-hetaryloxy)- or 2-(4-aryloxy)-phenoxyacetic acids VIII or the cyclohexenones IX, the novel herbicides may contain further herbicidal or growth-regulating active, ingredients having a different chemical structure, the antagonistic effect being retained.

Preparation Examples

EXAMPLE 1

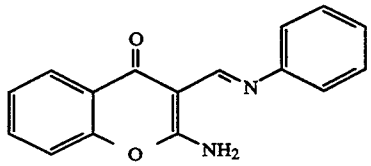

(Active Ingredient Example 1.006)

9.45 g (0.05 mol) of 2-amino-4-ox-4H-chromene-3-carbaldehyde [sic] were heated with 4.7 ml (0.05 mol) of aniline and 0.5 g of p-toluenesulfonic acid in 150 ml of toluene for 60 minutes under a water separator. The precipitate which separated out on cooling was filtered off under suction, washed with water and dried. Yield: 9.8 g (75%); mp. 210°–214° C.

EXAMPLE 2

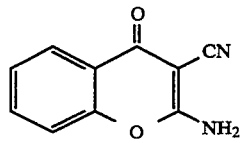

(Active Ingredient Example 1.010)

9.5 g (0.050 mol) of 2-amino-4-oxo-4H-chromene-3-carbaldehyde were heated to the boil with 3.8 g (0.055 mol) of hydroxylammonium chloride in 50 ml of formic acid for 45 minutes. 200 ml of water was added to the cooled solution and the precipitate was filtered off under suction, washed with water and dried. Yield: 8.4 g (90%), mp.>250° C.

EXAMPLE 3

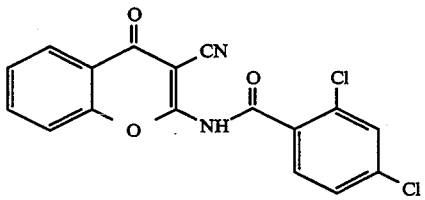

(Active Ingredient Example 1.028)

5.6 ml (0.04 mol) of 2,4-dichlorobenzoyl chloride were added to a mixture of 5.6 g (0.03 mol) of the product from Example 2 and 60 ml of pyridine, and stirring was carried out for 15 hours at 80° C. 300 ml of 5% strength hydrochloric acid were added to the cooled solution, the product being precipitated as solid. Yield: 6.5 g (60%); mp. 96°–98° C.

The active ingredients shown in Table 14 below can be prepared similarly to these process examples.

TABLE 14

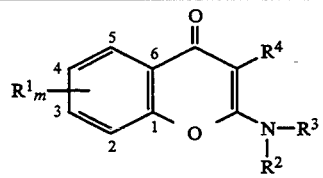

| Example No. | $R^1$ | $R^2$ | $R^3$ | $R^4$ | mp. (°C.) | Reference |
|---|---|---|---|---|---|---|
| 14.001 | H | H | H | CHO | 250(Z) | 1) |
| 14.002 | 6-CH$_3$ | H | H | CHO | 282–4 | 1) |
| 14.003 | 6-C$_2$H$_5$ | H | H | CHO | 246–9(Z) | 1) |
| 14.004 | 7-OCH$_3$ | H | H | CHO | 251–4(Z) | 1) |
| 14.005 | H | H | H | CH=N—OH | 290(Z) | |
| 14.006 | H | H | H | CH=N—C$_6$H$_5$ | 210–214 | |
| 14.007 | H | H | H | CH=N—(3-Cl—C$_6$H$_4$) | | |
| 14.008 | H | H | H | CH=N—(4-CH$_3$—C$_6$H$_4$) | | |
| 14.009 | H | H | H | CH=N—C$_6$H$_{11}$ | 182–184 | |
| 14.010 | H | H | H | CN | | 4) |
| 14.011 | 6-Br | H | H | CN | >340 | 2) |
| 14.012 | H | H | CO—CH$_3$ | CN | | |

TABLE 14-continued

| Example No. | $R^1$ | $R^2$ | $R^3$ | $R^4$ | mp. (°C.) | Reference |
|---|---|---|---|---|---|---|
| 14.013 | H | H | CO—CH$_2$—CH$_3$ | CN | | |
| 14.014 | H | H | CO—(CH$_2$—CH$_3$ | CN | | |
| 14.015 | H | H | CO—C(CH$_3$)$_3$ | CN | | |
| 14.016 | H | H | CO—CH$_2$—C(CH$_3$)$_3$ | CN | | |
| 14.017 | H | H | CO—(CH$_2$)$_{14}$—CH$_3$ | CN | | |
| 14.018 | H | H | CO—C$_3$H$_5$ | CN | | |
| 14.019 | H | H | CO—C$_6$H$_{11}$ | CN | | |
| 14.020 | H | H | CO—CH$_2$—Cl | CN | | |
| 14.021 | H | H | CO—CH$_2$—CH$_2$—Cl | CN | | |
| 14.022 | H | H | CO—CCl$_3$ | CN | | |
| 14.023 | H | H | CO—CF$_3$ | CN | | |
| 14.024 | H | H | CO—CH$_2$—C$_6$H$_5$ | CN | | |
| 14.025 | H | H | CO—C$_6$H$_5$ | CN | | |
| 14.026 | H | H | CO—(4-Cl—C$_6$H$_4$) | CN | | |
| 14.027 | H | H | CO—(2-Cl—C$_6$H$_4$) | CN | | |
| 14.028 | H | H | CO—(2,4-Cl$_2$—C$_6$H$_3$) | CN | 96-98 | |
| 14.029 | H | H | CO—(2-NO$_2$—C$_6$H$_4$) | CN | | |
| 14.030 | H | H | CO—(3-NO$_2$—C$_6$H$_4$) | CN | | |
| 14.031 | H | H | CO—(4-NO$_2$—C$_6$H$_4$) | CN | | |
| 14.032 | H | H | CO—NH—CH$_3$ | CN | | |
| 14.033 | H | H | CO—NH—CH$_2$—CH$_3$ | CN | | |
| 14.034 | H | H | CO—NH—C$_6$H$_5$ | CN | | |
| 14.035 | H | H | CO—NH—(3,4-Cl$_2$—C$_6$H$_3$) | CN | | |
| 14.036 | H | H | CS—NH—C$_6$H$_5$ | CN | | |
| 14.037 | H | | 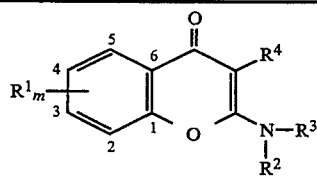 | CN | | |
| 14.038 | H | | =CH—C$_6$H$_5$ | CN | | |
| 14.039 | H | | —CH(2-Cl—C$_6$H$_4$) | CN | | |
| 14.040 | H | | =CH—(4-CH$_3$—C$_6$H$_4$) | CN | | |
| 14.041 | H | | =CH—(4-NO$_2$—C$_6$H$_4$) | CN | | |
| 14.042 | H | H | H | CO—NH$_2$ | | |
| 14.043 | 6-Br | H | H | CO—NH$_2$ | >325 | 2) |
| 14.044 | 4-i-C$_3$H$_7$ | H | H | CHO | | |
| 14.045 | H | H | H | CH=N—CH$_2$—C$_6$H$_5$ | | |

References
1) A. Nohara et al., J. Med. Chem. 28 (1985) 559.
2) G. P. Ellis et al., J. Chem. Soc. Perkin Trans I 1986, 1643.
3) U. Petersen et al., Liebigs Ann. Chem. 1976, 1659.
4) U.S. Pat. No. 3 932 466

Examples of the biological activity

The effect of various novel herbicides or herbicide combinations, consisting of herbicide and antidote compound, on the growth of desired and undesirable plants in comparison with the herbicidal active ingredient alone is demonstrated by the following biological examples from greenhouse experiments:

The culture vessels used were plastic flowerpots having a capacity of about 300 cm$^3$ and containing loamy sand with about 3.0% of humus as a substrate. The seeds of the test plants were sown shallowly and separately according to species and were moistened. Thereafter, the vessels were covered with transparent plastic covers until the seeds germinated uniformly and the plants had started to grow.

For the postemergence treatment, the test plants were first grown to a height of growth of from 3 to 20 cm, depending on the form of growth, and only then treated. The herbicides were suspended or emulsified in water as a distributing agent and were sprayed by means of finely distributing nozzles.

The test vessels were placed in a greenhouse, 18°-30° C. being preferred for warmth-loving species and 10°-25° C. for those from temperate climates.

The test period extended over 3-5 weeks. During this time, the plants were tended and their reaction to the individual treatments was recorded.

The damage to the test plants was evaluated on the basis of a scale from 0 to 100% in comparison with untreated control plants. 0 means no damage and 100 means complete destruction of the plants.

The plants used in the greenhouse experiments consisted of the following species:

| Botanical name | Common name |
|---|---|
| Setaria viridis | green foxtail |
| Triticum aestivum | winter wheat |
| Zea mays | Indian corn |

The following was used as an example herbicide of the cyclohexenone derivatives of the formula IX:

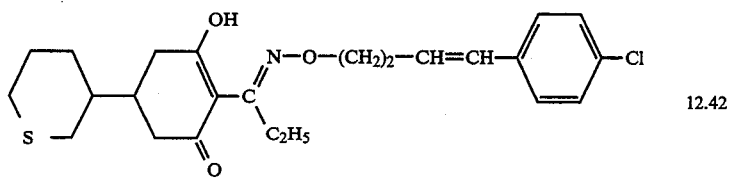

The active ingredient 12.42 was applied as an emulsion concentrate containing 200 g of active ingredient/l alone, with the addition of the amounts of solvents required for the antidotes, 80% by weight of cyclohexenone and 20% by weight of a surfactant (Emulphor EL*)) with 10% by weight of active ingredient.

All antidote compounds were formulated for the postemergence treatment as a mixture consisting of 80% by weight of cyclohexenone and 20% by weight of surfactant (Emulphor EL*)) with 10% by weight of active ingredient.
*)Ethoxylated castor oil The following Table documents the antidote activity of the novel compound 14.012.

This compound substantially improves the toleration of the active ingredient 12.42 by crops belonging to the Gramineae family (grasses).

TABLE 15

Improvement of the toleration of the herbicidal active ingredient 12.42 by crops through combination with the compound 14.012 in postemergence application in the greenhouse

| Application rate [kg/ha a.i.] | | Test plants and damage [%] | | |
|---|---|---|---|---|
| | | Crops | | |
| Herbicide 12.42 | Antidote 14.012 | Triticum aestivum[1)] | Zea mays[2)] | Undesirable plant Setaria viridis |
| 0.25 | — | 98 | 90 | 100 |
| 0.25 | 0.5 | 15 | 0 | 100 |

[1)]Urban variety
[2)]Lixis variety

TABLE 16

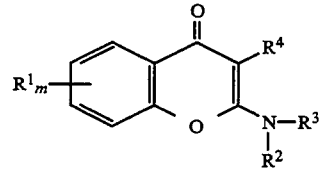

12.42

Improvement of the toleration of the herbicidal active ingredient 12.42 by crops through combination with the compound 14.043 in postemergence application in the greenhouse

| Application rate [kg/ha a.i.] | | Test plants and damage [%] | | |
|---|---|---|---|---|
| | | Crops | | |
| Herbicide 12.42 | Antidote 14.043 | Triticum aestivum[1)] | Zea mays[2)] | Undesirable plant Setaria viridis |
| 0.06 | — | 50 | 50 | 95 |
| 0.06 | 0.06 | 30 | 10 | 85 |

[1)]Urban variety
[2)]Lixis variety

We claim:
1. A 2-amino-4-oxo-4H-benzopyran of the formula I where
$R^1$ is hydrogen, hydroxyl, halogen, nitro, $C_1$-$C_6$-alkyl, $C_1$-$C_6$-alkoxy, $C_1$-$C_6$-haloalkyl, $C_1$-$C_4$-haloalkoxy, $C_1$-$C_4$-alkylthio or a group —$NR^5R^6$,
$R^5$ is hydrogen or $C_1$-$C_4$-alkyl,
$R^6$ is hydrogen, $C_1$-$C_4$-alkyl, —CO—$R^7$, —CS—$R^7$ or —$SO_2$—$R^8$,
$R^7$ is $C_1$-$C_{20}$-alkyl, $C_1$-$C_6$-haloalkyl, $C_3$-$C_8$-cycloalkyl, phenyl-$C_1$-$C_3$-alkyl, amino, $C_1$-$C_4$-alkylamino, di-$C_1$-$C_4$-alkylamino, phenyl or phenylamino where the phenyl radicals are each unsubstituted or carry from one to three of the groups stated for $R^1$,
$R^8$ is $C_1$-$C_4$-alkyl or is phenyl which may carry from one to three of the groups stated for $R^1$,
m is 0, 1 or 2, and the radicals $R^1$ may be different when m is 2,
$R^2$ is hydrogen or $C_1$-$C_4$-alkyl,
$R^3$ is a group —CO—$R^9$, —CS—$R^9$ or —$SO_2$—$R^{10}$,
$R^9$ has one of the meanings stated under $R^7$,
$R^{10}$ has one of the meanings stated under $R^8$.
2. A 2-amino-4-oxo-4H-benzopyran of the formula I as defined in claim 1, wherein $R^3$ is —C(O)$R^9$ and $R^4$ is cyano.

* * * * *

UNITED STATES PATENT AND TRADEMARK OFFICE
CERTIFICATE OF CORRECTION

PATENT NO. : 5,420,307
DATED : May 30, 1995
INVENTOR(S) : HAGEN et al.

It is certified that error appears in the above-indentified patent and that said Letters Patent is hereby corrected as shown below:

On the title page: Item [54] and Column 1, line 2,

"PREPARATAION" should read --PREPARATION--.

Column 58, claim 1, line 61, replace the period "." with the following:
-- , $R^4$ is cyano. --

Signed and Sealed this

Eighth Day of August, 1995

BRUCE LEHMAN

Attest:

Attesting Officer

Commissioner of Patents and Trademarks